(12) United States Patent
Oku et al.

(10) Patent No.: US 7,799,765 B2
(45) Date of Patent: Sep. 21, 2010

(54) ASSOCIATION COMPOUND OF TREHALOSE OR MALTITOL WITH METAL ION COMPOUND

(75) Inventors: Kazuyuki Oku, Okayama (JP); Michio Kubota, Okayama (JP); Shigeharu Fukuda, Okayama (JP); Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 957 days.

(21) Appl. No.: 10/486,328

(22) PCT Filed: Aug. 8, 2002

(86) PCT No.: PCT/JP02/08132

§ 371 (c)(1),
(2), (4) Date: Feb. 10, 2004

(87) PCT Pub. No.: WO03/016325

PCT Pub. Date: Feb. 27, 2003

(65) Prior Publication Data

US 2004/0209841 A1    Oct. 21, 2004

(30) Foreign Application Priority Data

| Aug. 10, 2001 | (JP) | 2001-245083 |
| Nov. 2, 2001 | (JP) | 2001-338458 |
| Dec. 26, 2001 | (JP) | 2001-395153 |
| Jul. 4, 2002 | (JP) | 2002-195390 |

(51) Int. Cl.
*A61K 31/715* (2006.01)

(52) U.S. Cl. ............ 514/53; 514/54; 536/123.13; 536/123.1; 536/124; 424/489

(58) Field of Classification Search .......... 514/53, 514/54; 536/123.13, 123.1, 124; 424/489
See application file for complete search history.

(56) References Cited

U.S. PATENT DOCUMENTS 3,823,129 A   7/1974  Kalb et at.
4,408,041 A   10/1983 Hirao et al.
5,762,961 A   6/1998  Roser et al.
6,649,386 B2 * 11/2003 Roser ................ 435/188
6,669,963 B1 * 12/2003 Kampinga ........... 424/499

FOREIGN PATENT DOCUMENTS

| EP | 813 820 A1 | 12/1997 |
| EP | 888 916 A2 | 10/1998 |
| EP | 0 983 727 A2 | 3/2000 |
| GB | 1 383 724 A | 2/1974 |
| GB | 2 097 004 A | 10/1982 |
| JP | 03067571 A * | 3/1991 |
| JP | 4-360645 A | 12/1992 |
| JP | 7-111863 A | 5/1995 |
| JP | 7-250613 A | 10/1995 |
| JP | 8-183996 A | 7/1996 |
| JP | 11-348719 A | 12/1999 |
| WO | WO 02/24832 A | 3/2002 |

OTHER PUBLICATIONS

Cook et al. (Carbohydrate Research, (1973) vol. 31, pp. 265-275).*
Lieser et al. (Ann. (1937), 532, 89-94) (Abstract Sent).*
Nagy et al. (Acta Chimica Hungarica (1988), 125 (3), 403-13 (Abstract Sent).*
Izumida et al.; JP 03067571 A, Mar. 22, 1991 (Abstract sent).*
"Jikken-Kagaku-Kohza (Course of experimental chemistry) 5", edited by the Chemical Society of Japan, (1991), pp. 221-224.
"Jikken-Kagaku-Kohza (Course of experimental chemistry) 5", edited by the Chemical Society of Japan, (1991), pp. 302-312.
Bradbury, J.H. et al., "Determination of the Structures of Trisaccharides by $^{13}$C-N.M.R. Spectroscopy", Carbohydrate Research, vol. 126, (1984), pp. 125-126.
Cook. J. et al., "Calcium Interactions With $_o$-Glucans: Crystal Structure of $_{\alpha,\alpha}$-Trehalose-Calcium Bromide Monohydrate", Carbohydrate Research, vol. 31, (1973), pp. 265-275.

* cited by examiner

*Primary Examiner*—Shaojia Anna Jiang
*Assistant Examiner*—Michael C Henry
(74) *Attorney, Agent, or Firm*—Browdy and Neimark, PLLC

(57) ABSTRACT

The object of the present invention is to provide a composition of metal ion compound whose inherent and unsatisfactory properties for its industrial application such as deliquescence, reducing power, oxidizing power, low solubility in water, etc., are improved; and their preparation and uses. The present invention solves the above object by providing an associate of trehalose or maltitol and a metal ion compound or bittern component, and their preparation and uses.

4 Claims, 13 Drawing Sheets

ASSOCIATION COMPOUND OF TREHALOSE OR MALTITOL WITH METAL ION COMPOUND

TECHNICAL FIELD

The present invention relates to novel associates of saccharides and metal ion compounds, and more particularly, to associates of trehalose or maltitol and metal ion compounds.

BACKGROUND ART

Compared with carbon, oxygen, hydrogen, nitrogen, etc., metal elements such as sodium, potassium, calcium, magnesium, iron, copper, zinc, nickel, etc., are not necessary in a large amount for living bodies. However, these are essential elements for keeping normal biological functions. Such metal elements are usually administrated with living bodies in the form of a compound comprising ionized metal elements (metal ion compounds) such as salts, and exert respective functions in the bodies.

It is known that magnesium and calcium are minerals involving enzymatic reactions in human bodies, and are required in relatively large amounts. Deficiencies of magnesium and calcium cause of bone-thinning osteoporosis and osteomalacia because these metal elements are present in relatively large amounts in the bone of living bodies. Recently, a deficiency of magnesium has been recognized as a cause of diseases such as diabetes and hypertension.

Magnesium is an essential mineral for plants, and is generally supplied to plants as a fertilizer, with a nitrogen, phosphorus, and potassium, in a liquid or solid form and used for their growth. It is known that a deficiency of magnesium causes its a deficiency disease. While various metal elements are essential to living bodies as described above, there is a case that metal ion compounds such as salts induce unpleasant tastes depending on the amount when orally administrated. Therefore, the problem of metal ion compounds in the field of food industries is recognized mainly as their unpleasant tastes when orally administrated, and various studies have been done to solve the problem.

The present inventors have widely studied mainly on the developments and uses of novel food materials with the focus on saccharides and saccharide-related substances. As a part of the study, the present inventors have studied on compositions comprising saccharides and metal ion compounds for their novel and effective uses in food industries. In the study, the present inventors found the facts that metal ion compounds, usually used in the field of foods, had unpleasant properties such as deliquescence, reducing power, oxidizing power, low solubility in water, etc., for the production and preservation of foods or their raw materials; that the unpleasant properties have been usually presumed to be inherent and unimproved properties of metal ion compounds; and that they have never been recognized as problems to be solved. The present inventors thought that the development of preparations of metal ion compounds with improved unpleasant characteristics and their supplies would greatly contribute to the food industries.

The present invention solves a quite novel object raised on the basis of original concept of the present inventors by providing preparations comprising metal ion compounds or bittern components whose inherent and inconvenient properties for industrial application such as deliquescence, reducing power, oxidizing power, low solubility in water, etc., are improved.

DISCLOSURE OF INVENTION

The present inventors began to studies with the aim to solve the above object by putting their original knowledge of the uses of saccharides to account. At first, the changes of inherent properties of metal ion compounds were widely investigated by allowing them to coexist with saccharides in various combinations. As a result, it was revealed that two non-reducing saccharides, trehalose and maltitol, exhibited functions of improving deliquescence of metal ion compounds, increasing their solubility in water, and suppressing their oxidative/reductive reaction, by allowing them to coexist with metal ion compounds, and that the functions were remarkably superior to those of other saccharides. Successively, in order to investigate the mechanism of exercising above functions, interaction between trehalose or maltitol and metal ion compounds was analyzed in detail on the molecular level. As a result, it was revealed that trehalose and maltitol formed associates with metal ion compounds, and that the resulting associates showed the different properties described above from those of intact metal compounds. From the results described above, it was revealed that associates, which are obtainable by allowing trehalose or maltitol to coexist with metal ion compounds, exhibited great merits in food industries in comparison with conventional preparations of metal ion compounds. In the case of bittern components, a concrete example of such metal ion compounds comprising magnesium ion compounds and/or calcium ion compounds, it also formed associates and exhibited great merits. The present invention was accomplished based on the original knowledge described above by the present inventors. By way of parenthesis, as regards associates of trehalose and salts, a crystalline associate, constructed with trehalose and calcium bromide in a molar ratio of 1:1, has been reported by William J. Cook et al. in "*Carbohydrate Research*", Vol. 31, pp. 265-275 (1973). The crystalline associate was found in the process of their studies to solve the mechanism of dental plaque formation in the mouth. The industrial uses of an associate of trehalose and calcium bromide or its crystalline form are not suggested by their knowledge. Therefore, the present invention firstly discloses associates of trehalose or maltitol and metal ion compounds except calcium bromide, or bittern components, which are useful in various industries such as food processing, their preparations and uses.

As described above, the present invention solves the above object by providing associates of trehalose or maltitol and either metal ion compounds or bittern components, and their preparations and uses.

BEST MODE FOR CARRYING OUT THE INVENTION

Figure 1:
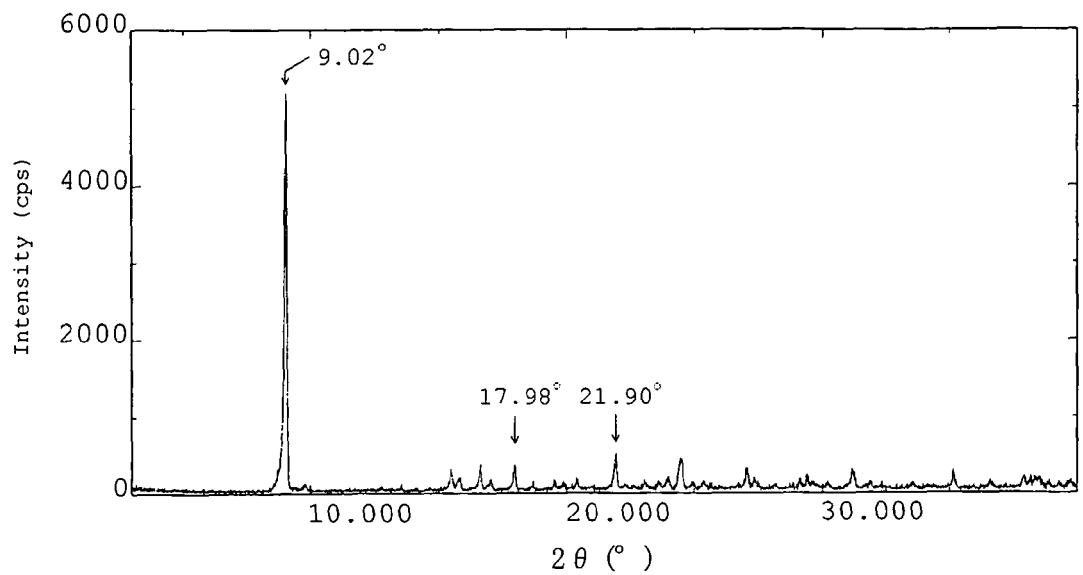
FIG. 1 shows an X-ray diffraction pattern of a crystalline associate of trehalose and calcium chloride (molar ratio of 1:1).

The present invention relates to associates of trehalose or maltitol and metal ion compounds except calcium bromide or bittern components, and to their preparations and uses. The term "trehalose" as referred to as in the present invention means α,α-trehalose, a disaccharide which two glucose molecules are bound together at their reducing groups via the α,α-linkage. The term "maltitol" as referred to as in the present invention means a sugar alcohol obtainable by reducing maltose, a disaccharide which two glucose molecules are bound via the α-1,4 glucosidic linkage. In the present invention, trehalose and maltitol are not restricted by their purity and form (liquid, amorphous powder, hydrous crystalline powder, anhydrous crystalline powder, etc.) as far as they each form associates with metal ion compounds described later. Trehalose and maltitol, usable in the present invention, can be prepared by conventional methods, however, commercially available ones can be arbitrarily used. For example, "TREHA®", a food grade hydrous crystalline trehalose powder (a trehalose content of 98% or higher by HPLC analysis), commercialized by Hayashibara Shoji, Inc., Okayama, Japan, can be used as a commercially available trehalose. "MABIT®", a food grade syrup comprising maltitol (74% or higher on a dry solid basis, maltitol content of 75% or higher to the total sugar by HPLC analysis); and "Crystalline MABIT", a food grade anhydrous crystalline maltitol (a moisture content of 1.5% or lower, a maltitol content of 99% or higher by HPLC analysis) can be used as a commercially available maltitol.

The term "metal ion compound" as referred to as in the present invention means a compound having a metal ion as a cation in compounds having an ionic bond between cation and anion, and includes a salt, alkali, or complex. In the present invention, any metal ion compounds except calcium bromide, which can form associates with trehalose or maltitol, can be advantageously used. For example, metal ion compounds comprise one or more metal ions having monovalent (univalent) or more ionic charges as cation, particularly, one or more metal ions of the groups 1 to 16 of the periodic table of the elements, more particularly, one or more metal ions selected from lithium, sodium, potassium, rubidium, etc. of the group 1, beryllium, magnesium, calcium, strontium, etc. of the group 2, scandium, yttrium, etc. of the group 3, titanium, zirconium, hafnium, etc., of the group 4, vanadium, niobium, tantalum, etc., of the group 5, chromium, molybdenum, tungsten, etc., of the group 6, manganese, technetium, rhenium, etc., of the group 7, iron, ruthenium, etc., of the group 8, cobalt, rhodium, etc., of the group 9, nickel, palladium, etc., of the group 10, copper, silver, etc., of the group 11, zinc, etc., of the group 12, aluminum, gallium, etc., of the group 13, germanium, etc., of the group 14, antimony, etc., of the group 15, and polonium, etc., of the group NO:16. In those compounds, metal ion compounds, comprising one or more metal ions selected from the groups of alkali earth metal ions such as calcium, magnesium, strontium ions, etc., metal ions belonging to transition elements such as ferrous, copper, nickel, manganese, zinc ions, etc., and alkali metal ions such as sodium, potassium, etc., have a relatively remarkable usefulness as described later in detail as associates. Since metal compounds, comprising metal ions having divalent or more charges, are more useful, those are especially useful in the present invention. One or more anions selected from halogen ions such as fluorine ion, chlorine ion, and bromine ion (except in the case of metal ions having calcium ion as counter ion), inorganic anions such as sulfate ion, sulfite ion, monohydrogen sulfate ion, thiosulfate ion, carbonate ion, bicarbonate ion, nitrate ion, phosphate ion, mono-hydrogen phosphate ion, di-hydrogen phosphate ion, chlorite ion, hydroxide ion, and ammonium ion, and organic anions such as acetate ion, lactate ion, citrate ion, fumaric ion, and malate ion, can be used for anions of metal ion compounds in the present invention. Since metal ion compounds having inorganic anions are relatively useful as described below, metal ion compounds comprising inorganic anions can be advantageously used. Regarding the application of metal ion compounds of the present invention to living bodies, physiologically acceptable metal ion compounds are desirably used. Hereinafter, the term "metal ion compounds" means all metal ion compounds except for calcium bromide.

The term "associates" as referred to as in the present invention means substances associating trehalose or maltitol and metal ion compounds via a direct interaction. Such associates in the present invention are substantially constructed by trehalose or maltitol and metal ion compounds. The word "direct interaction" as referred to as in the present invention means hydrogen bond, van der Waals force, ionic bond, or coordinate bond, and includes those in solid, gas, liquid or paste state. Also, the word "substantially constructed by trehalose or maltitol and metal ion compounds", as referred to as in the present invention means associates which are usually constructed by trehalose or maltitol and metal compounds, and depending on circumstances, further means those which comprise other molecules such as bound water as constituents. Metal ion compounds in the above associates are usually being associated with trehalose or maltitol in a neutralizing form (for example, salts, etc.) of metal ion and its counter ion. Depending on circumstances, metal ions can associate with trehalose or maltitol, and the counter ion bounds to neutralize the resulting associates. The associates of the present invention can be identified as follows: Associates formed in solution can be identified by nuclear magnetic resonance (NMR) method described, for example, in "*Jikken-Kagaku-Kohza* (Course of experimental chemistry) 5", edited by The Chemical Society of Japan, published by Maruzen Co., Ltd., pp. 221-224 (1991). Associates can be identified by analyzing a solution comprising an associate of the present invention and a solution not comprising the associate, for example, comprising only trehalose or maltitol by using NMR, comparing the relaxation time of constituent atoms, and detecting the phenomenon that atoms of the associate show shorter relaxation times. Further, such associates can be identified by the fact that one or more signals assigned with chemical shifts (ppm) show signals with different chemical shifts in comparison with the corresponding signals observed in the case of using trehalose or maltitol alone. Furthermore, the associates can be also identified by crystallizing them in solutions, isolating the resulting crystals, and analyzing their crystallographic structure. Specifically, the associates of the present invention can be identified by the steps of analyzing their X-ray diffraction patterns, and comparing them with those of crystalline trehalose, maltitol or crystalline metal ion compound alone, respectively; and confirming the fact that X-ray diffraction patterns of the associates are not agreed with any of those obtained from trehalose or maltitol and metal ion compound, and combination patterns thereof. The associates of the present invention, described above, includes metal ion compounds (or metal ions) in molar ratios to trehalose or maltitol of, usually, 0.5 or higher but five or lower, desirably, one or higher but four or lower. As in the case of crystalline associates of trehalose and calcium chloride, which are described in detail in Examples later described, the associates may give a prescribed molar ratio of trehalose or maltitol to a metal ion compound, such as about one or two.

The associates of the present invention can be formed by mixing trehalose or maltitol with metal ion compounds. The mixing can be done by contacting trehalose or maltitol with metal ion compounds. Usually, it is preferable to mix them using a same solvent under a condition which the both components are dissolved. Water, ethanol, methanol, acetonitrile, dimethylsulfoxide, dimethylformamide, and acetic acid can be used as the solvent. In the case of preparing the associates to apply to living bodies in the fields of foods, cosmetics, and pharmaceuticals, physiologically acceptable solvents such as water and ethanol can be desirably used. In the case of using a hydrous form of trehalose, metal ion compounds, or inherently deliquescent metal ion compounds such as calcium chloride, it is possible to form desired associates by mixing them in solid forms. Although the proportion of trehalose or maltitol to metal ion compounds depends on the kind of metal ion compounds, the molar ratio of metal ion compounds to trehalose or maltitol can be preferably set to in the range of, usually, 0.01 or higher but 100 or lower, desirably, 0.1 or higher but 10 or lower. As in the case of associates of trehalose and calcium chloride, which are described later in detail in Examples; the associates can be obtained efficiently by mixing trehalose or maltitol and metal ion compounds in prescribed molar ratios such as about one or two.

The associates of trehalose or maltitol and metal ion compounds, formed as described above, can be used intact, for example, as solution forms; and they can be also used as isolated forms. For example, extraction, filtration, concentration, centrifugation, dialysis, precipitation, crystallization, hydrophobic chromatography, gel-filtration chromatography, and affinity chromatography can be used as the method for isolating the associates.

The associates, formed as described above, or fractions containing the same can be collected by methods such as crystallization, precipitation, concentration, and drying (including a spray drying, drying in vacuo, and freeze-drying). Depending on the kinds of metal ion compounds, the associates, obtainable by the above methods, have excellent properties in comparison with conventional preparations of metal ion compounds as follows:

(1) Decreased Deliquescence

Alkaline earth metal halides including calcium chloride have deliquescent properties. The deliquescent properties of the metal ion compounds are remarkably decreased by forming associates with trehalose or maltitol. Therefore, there is a feature of having a satisfactory handleability in the associates of the present invention, which comprise metal ion compounds having an inherent deliquescence. Such properties can be advantageously applied to produce deliquescence-suppressing agents. For example, the hygroscopicities of marine products comprising bittern components can be suppressed.

(2) Inhibition of Forming Hardly Soluble or Insoluble Metal Ion Compounds

In some cases, metal ions form salts having a low solubility in water depending on a kind of counter ions as in the case of calcium phosphate. When a counter ion, which forms hardly soluble or insoluble salts with such metal ions, is added to a solution comprising such metal ions, a substance (salt) having a low solubility is rapidly formed and precipitated. The formation of such a hardly soluble or insoluble salt can be suppressed by forming associates of a compound comprising such a metal ion and trehalose or maltitol before the formation of a hardly soluble or insoluble salt which is formed by a water-soluble compound comprising such a metal ion. Therefore, associates of a compound, comprising a metal ion which is inherently capable of forming a hardly soluble or insoluble salt, and trehalose or maltitol can be used as a preparation whose precipitation or clouding in water is suppressed. Such properties can be applied to produce a precipitation-suppressing agent for hardly soluble or insoluble salts.

(3) Improved Solubility in Water

Metal ion compounds, which are in an associate form with trehalose or maltitol, have, in many cases, a higher solubility in water than those of inherent metal ion compounds. For example, transition metal ion compounds such as manganese salts, nickel salts, iron salts, and copper salts; calcium salts, magnesium salts, and sodium salts are improved in their solubility in water when associated. Therefore, trehalose and maltitol can be advantageously used as a solubility-improving agent for those metal ion compounds. Further, associates of those metal ion compounds and trehalose or maltitol can be advantageously used in the fields of foods, cosmetics, and pharmaceuticals, desiring the provision of the solution comprising metal ion compounds in high concentrations.

The above properties of the associates, described in items (2) and (3), were revealed to be of forming water-soluble chelate-like compounds by extensive studies by the present inventors. It was also revealed that the associates could be advantageously used for the following uses because they had no toxicity and a relatively high safety, and gave a relatively low influence on the environment.

<1> Since the solubility in aqueous solutions of metal ion compounds, specifically, calcium ion compounds can be improved by forming associates with trehalose or maltitol, trehalose and maltitol can be used for preventing the precipitation and clouding of beverages, comprising such compounds, such as soft drinks, isotonic drinks, and mineral-supplementing infusion solutions.

<2> Precipitation of hardly soluble salts, specifically, magnesium ion compounds, formed when cooking boiled foods and winter cuisine in the pot, can be suppressed by forming associates with trehalose or maltitol. As a result, the formation of scum can be vastly suppressed.

<3> Precipitation of hardly soluble salts, specifically, magnesium-fatty acid salts can be suppressed by forming associates with trehalose or maltitol when a soap is dissolved in hard water comprising metal ion compounds. As a result, the formation of a soap scum can be vastly suppressed, and the foaming and washing power of soapy solutions are hardly deteriorated.

<4> Precipitation of hardly soluble salts, specifically, iron salts and magnesium salts, which are inherently formed when hard water is left or boiled, can be suppressed by forming associates with trehalose or maltitol. As a result, the clouding of water and the formation of scales can be suppressed.

<5> In the case of hardly soluble or insoluble substances formed by associating metal ion compounds with organic substances except for saccharides, for example, glycosides and polyphenols, the solubility in water of the organic substances can be improved by associating the metal ion compounds with trehalose or maltitol.

<6> Dirt resulted from metal ion compounds can be prevented and easily removed by washing by forming associates of metal ion compounds and trehalose or maltitol. Therefore, trehalose and maltitol can be advantageously used as a preventing agent, removing agent, washing agent, and bed-bath agent for pollution by metal ion compounds. Those agents can be preferably used for preventing or removing pollution of surfaces of glasses, metals, cars, houses, clothes, and bodies.

<7> In the case of tartars or dental plaques resulting from calcium ion compounds and magnesium ion compounds, their adhesion can be suppressed and their dissolution can be promoted by associating the metal ion compounds with trehalose or maltiol. Therefore, trehalose and maltitol can be advantageously used for mouth wash and dental paste.

(4) Suppression of Oxidative or Reductive Reaction

Ions of transition metals such as iron and copper and other metals may be oxidized or reduced depending on conditions. It is possible that such oxidative and reductive reactions deteriorate other substances which are coexisted with such ions. When such metal ion compounds form associates with trehalose or maltitol, their oxidative or reductive reactivities are usually suppressed. Therefore, associates of metal ion compounds, which have potency of being oxidized or reduced, such as iron and copper salts; and trehalose or maltitol can be advantageously used as metal ion compound preparations without deteriorating qualities of other substances. By the properties, the oxidation and deterioration of substances which are easily oxidized or deteriorated by the coexistence of a relatively low amount of iron salts or copper salts, for example, vitamins such as L-ascorbic acid (hereinafter, may be briefly called "ascorbic acid") and tocopherols, highly unsaturated fatty acids such as eicosapentaenoic acid (EPA) and docosahexanoeic acid (DHA), flavors, and colorings can be suppressed by admixing with trehalose or maltitol to form associates.

Powdery products comprising associates of trehalose or maltitol and metal ion compounds which comprise magnesium ion compounds and/or calcium ion compounds (hereinafter, may be briefly called "powdery product comprising associates") can be prepared by the steps of mixing trehalose or maltitol with metal ion compounds which comprise magnesium ion compounds and/or calcium ion compounds, forming associates, and then pulverizing the associates. It is preferable to mix trehalose or maltitol and a metal ion compound(s) comprising a magnesium ion compound and/or a calcium ion compound, which are dissolved in an aqueous solvent, to form associates. The molar ratio of metal ion compound(s) comprising a magnesium ion compound and/or a calcium ion compound to trehalose or maltitol is preferable to be set in the range of, usually, 0.001-10, desirably, 0.01-5. In the case of the molar ratio of lower than 0.001, it is inconvenient to use the mixture as a mineral-enriched agent or the like because of a low content of an associate comprising a magnesium ion compound and/or a calcium ion compound. In the case of the molar ratio of higher than 10, powdery products comprising the associate, which is prepared using the mixture, are insufficiently improved in deliquescence.

Metal ion compounds comprising magnesium ion compounds and/or calcium ion compounds can be prepared by mixing commercially available magnesium ion compounds and calcium ion compounds in a proper proportion. Bittern is an example comprising the both in a mixed form. Optionally, other metal ion compounds and organic substances such as saccharides and saccharide-related substances can be added to such bittern.

Bittern is generally produced by the steps of concentrating seawater by a heating method and/or ion exchange method, precipitating sodium chloride, separating the resulting sodium chloride, and collecting the residual solution. Bittern has a strong pungent smell and unpleasant taste such as bitter taste, and comprises magnesium ion compounds as a major component and calcium ion compounds, potassium ion compounds, and sodium ion compounds as other components. Bittern has been used as materials for producing magnesium salts and potassium salts, flavor-improving agents for soymilks, and coagulating agents for producing "tofu" (soybean curd).

Bittern components mean metal ion compounds comprising bittern and comprises at least magnesium ion compounds and/or calcium ion compounds. Usually, bittern is commercialized in a liquid form and comprises, for example, 17.5% (w/w) of magnesium chloride, 8.1% (w/w) of calcium chloride, 3.6% (w/w) of potassium chloride, 2.9% (w/w) of sodium chloride as components. Dried bittern powders, which are obtainable by concentrating intact bittern followed by crystallizing or drying and pulverizing, have a relatively strong hygroscopicity and easily change to a liquid form by their deliquescence during preservation under a relatively high humid condition.

The associates, formed by the method of the present invention, can be collected in a powdery form (in addition to liquid- and paste forms) by the methods such as crystallization, fractional precipitation, concentration, and drying (including spray drying, drying in vacuo, and freeze-drying). Undesirable properties such as deliquescent property, reducing power, oxidizing powder, and low solubility in water for industrial handling of conventional powder preparation of metal ion compounds comprising magnesium ion compounds and/or calcium ion compounds are improved in the powdery products comprising the associates thus obtained. Therefore, the powdery products comprising associates have satisfactory characteristics.

The associates and powdery products comprising the same of the present invention, which exhibit the action described above, are very useful in various fields using metal ion compounds or bittern as materials, ingredients, and products, for example, foods (including beverages), agricultural and marine products, cosmetics, pharmaceuticals, commodities, chemical industries, and productions of materials and ingredients, used in these fields. They can be used in an isolated form and optionally in a composition form along with other ingredients, for example, one or more fillers and excipients such as calcium carbonate, calcium phosphate, lactose, sugar alcohols, cyclic saccharides, dextrin, starch, and cellulose. Other ingredients, which can be used along with the associates or powdery products comprising the associates of the present invention, are desirable to be biologically acceptable ingredients in the case of using such composition to living bodies. In the case of using in the field of foods, the associates and powdery products comprising the same of the present invention can be used along with, for example, sweeteners such as sucrose, glucose, maltose, L-fucose, L-rhamnose, stevia, *Glycyrrhiza glabla*, L-aspartyl L-phenylalanine methyl ester, glycyrrhizinate, and sucralose, acidifiers such as adipic acid, citric acid, glucono delta lactone, acetic acid, tartaric acid, fumaric acid, and lactic acid, seasonings such as sodium aspartate, alanine, citric acid, glutamic acid, theanine, and sodium chloride, one or more colorings, flavors, reinforcement, swelling agents, preservatives, disinfectants, oxidation-preventing agents, decolorant, paste agents, stabilizing agents, and emulsifiers, which are generally used in foods.

Also, the associates and powdery products comprising the same of the present invention can be used for foods; concrete examples are various seasonings such as table salt, soy sauce, powdered soy sauce, "miso" (bean paste), "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-zu" (powdered vinegar for sushi), "chuka-no-moto" (an instant mix for Chinese dish), "tentsuyu" (a sauce for Japanese deep fat fried food), "mentsuyu" (a sauce for Japanese vermicelli), bouillon, sauce, ketchup, "yakiniku-no-tare" (a sauce for Japanese grilled meat), curry roux, instant stew mix, instant soup mix, "dashi-no-moto" (an instant stock mix), nucleic acid seasoning, mixed seasoning, "mirin" (a sweet sake), "shin-mirin" (a synthetic mirin), table sugar, and coffee sugar; various "wagashi" (Japanese cakes) such as "senbei" (a rice cracker), "arare" (a rice cake cube), "okoshi" (a millet and rice cake), "mochi" (a rise paste) and the like, "manju" (a bun with a bean-jam), "uiro" (a sweet rice jelly), "ann" (a bean-jam) and the like, "yokan" (a sweet jelly of beans), "mizu-yokan" (a soft azuki-bean jelly), "kingyoku" (a kind of yokan), jelly, pao de Castella, and "amedama" (a Japanese toffee); western confectioneries such as a bun, biscuit, cracker, cookie, pie, pudding, butter cream, custard cream, cream puff, waffle, sponge cake, doughnut, chocolate, chewing gum, caramel, and candy; frozen desserts such as an ice cream and sherbet; syrups such as a "kajitsu-no-syrup-zuke" (a preserved fruit) and "korimijtsu" (a sugar syrup for shaved ice); pastes such as a flour paste, peanut paste, fruit paste, and spread; processed fruits and vegetables such as a jam, marmalade, "syrup-zuke" (fruit pickles), and "toka" (conserves); pickles and pickled products such as a "fukujin-zuke" (red colored radish pickles), "bettara-zuke" (a kind of whole fresh radish pickles), "senmai-zuke" (a kind of sliced fresh radish pickles), and "rakkyo-zuke" (pickled shallots); premix for pickles and pickled products such as a "takuan-zuke-no-moto" (a premix for pickled radish), and "hakusai-zuke-no-moto" (a premix for fresh white rape pickles); meat products such as a ham and sausage; products of fish meat such as a fish ham, fish sausage, "kamaboko" (a steamed fish paste), "chikuwa" (a kind of fish paste), and "tempura" (a Japanese deep-fat fried fish paste); dried marine products such as a dried seaweed, dried whole fish, opened and dried fish; "chinmi" (relish) such as a "uni" (urchin), "ika-no-shiokara" (salted guts of squid), "su-konbu" (processed tangle), "saki-surume" (dried squid strips), "fugu-no-mirin-boshi" (a dried mirin-seasoned swellfish); "tsukudani" (foods boiled down in soy sauce) such as those of laver, edible wild plants, dried squid, small fish, and shellfish; daily dishes such as a "nimame" (cooked beans), potato salad, and "konbu-maki" (a tangle roll); milk products such as yoghurt and cheese; canned and bottled products such as those of fish meat, meat, fruit, and vegetable; alcoholic beverages such as a sake, synthetic sake, liqueur, and western liquor; soft drinks such as a coffee, tea, cocoa, juice, isotonic drink, mineral-supplement drink, mineral-enriched drink, carbonated beverage, fruit juice beverage, sour milk beverage, beverage containing a lactic acid bacterium, vegetable juice, and soymilk; instant food products such as instant pudding mix, instant hot cake mix, "sokuseki-shiruko" (an instant mix of azuki-bean soup with rice cake), and instant soup mix; solid foods for babies, foods for therapy; health drinks such as a ginseng extract, bamboo leaf extract, plum extract, pine leaf extract, turtle extract, chlorella extract, aloe extract, propolis extract; and other foods and beverages such as peptide foods, frozen foods, healthy foods, viable cell of lactic acid bacteria and yeast, and royal jelly; mineral enrichments comprising calcium and/or magnesium, growth-promoting agent for *Bacillus natto*, flavor-improving agent, flavor-improving agent for soymilk, and coagulating agent for the production of "tofu" (bean curd).

In the case of using the associates and powdery products comprising the same of the present invention in the field of agricultural and marine products, they can be advantageously used intact or as a composition form comprising other additional ingredients for feeds and pet foods for animals or nutritional supplements or activating agents for plants. One or more ingredients, which are generally used in the following respective fields, for example, feeds or feed ingredients such as bagasse, corncob, rice straw, hay, grain, wheat flour, starch, oil meal, wasted sugar, wheat bran, bean cake, various fermentation cake, chip, and leaf and the like; ingredients for nutritional supplements such as nitrate, ammonium salts, urea, phosphate, and potassium salts can be used as other ingredients which can be added to the composition.

Also, they can be advantageously used in various materials for concentrated feeds, feed mixtures, and pet food mixtures for domestic creatures, for example, domestic animals, poultry, honeybee, silkworm, insects, and fishes; and nutrition-supplements and activating agents for plants, for example, crops such as grains and potatoes and the like, vegetables, tea plants, fruit trees, planting of garden and roadside trees, and grass of golf course.

In the case of using the associates and powdery products comprising the same in the present invention in a composition form in the fields of cosmetics and pharmaceuticals, one or more of the following ingredients can be used conventionally in those fields, for example, moisture-retaining agents, detergents, colorings, flavors, enzymes, hormones, vitamins, ultraviolet rays (UV)-absorbing agents, UV-shielding agents, solvents, stabilizing agents, plasticizers, suaving agents, solubilizing agents, reducing agents, buffers, sweeteners, bases, vaporization-assisting agets, adsorbents, corrigents, synergists, binders, suspending agents, anti-oxidation agents, brightening agents, coating agents, dampers, refrigerants, softeners, emulsifiers, excipients, antiseptic agents, and preservatives.

Also, they can be advantageously used for specific products, for example, cosmetics such as a milky lotion, cream, shampoo, rinse, treatment, lipstick, rouge, lip cream, lotion, bath agent, and tooth paste; amenities such as a tobacco and cigarrette; pharmaceuticals such as an internal liquid medicine, tablet, slave, troche, cod-liver oil in the form of drop, oral refrigerant, cachou, gargle (mouthwash), magnesium supplement, and mineral-enrichment; and stabilizing agents for various enzymes.

In order to produce the compositions described above, it is preferable to add the associates or the powdery products comprising the same to the compositions in the range of, usually, 0.00001-75% (w/w), desirably, 0.0001-50% (w/w), more desirably, 0.001-25% (w/w), on a dry solid basis (d.s.b.).

Since trehalose and maltitol suppress the formation of scum during the cooking of meat and vegetables, and of soap scum and scales, they can be advantageously used as a formation-suppressing agent for scum, soap scum, and scales for seasonings for boiled foods and winter cuisines in pot, mineral water, bath agents, and soaps.

Further, trehalose suppresses the elution of magnesium ion compounds from food materials such as meats and vegetables when cooked. Therefore, trehalose can be advantageously used as an elution-suppressing agent for magnesium ion compounds for seasonings for boiled foods and winter cuisines in pot. The elution of magnesium ion compounds, which are mineral components, from food materials is suppressed by using these seasonings. Therefore, the seasonings can be used to retain nutritional components and to exert inherent tastes of food materials.

The following Experiments 1 to 3 explain the fact that trehalose and maltitol form associates with various metal ion compounds and bittern components. Experiments 4 to 8 explain the usefulness of the associates. Further, Experiments 9 to 12 explain the suppressing effect of trehalose and maltitol on the formation of scum during cooking, and the suppressing effect of trehalose on the elution of magnesium ion compounds.

Experiment 1

Associate Formed from Trehalose and Calcium Chloride

Experiment 1-1

Crystalline Associate Formed from Trehalose and Calcium Chloride

Experiment 1-1(a)

Isolation of Crystalline Associate

One hundred and forty-seven grams (one mole) of calcium chloride dehydrate was placed in a 1-liter glass beaker, admixed with 250 grams of deionized water, and dissolved completely by heating. Under continuous heating condition, 378 grams (one mole) of crystalline trehalose dihydrate (hereinafter, called simply "hydrous crystalline trehalose") was added to the solution and dissolved completely. After stopping the heating and preserving the beaker at room temperature (about 25° C.) for two days, precipitates comprising crystals were observed in the bottom of the beaker. The crystals were transferred to a bucket-type centrifugal separator and washed by spraying thereto an appropriate amount of water and collecting the resulting crystals. The collected crystals were dried in vacuo at 40° C. for four hours. Further, the crystals were dried well by preserving in a desiccator containing phosphorous pentoxide at room temperature for 20 hours. As a result, about 200 grams of a white crystalline powder was obtained.

Two hundred and ninety-four grams (two moles) of calcium chloride dehydrate was placed in a 1-liter glass beaker, admixed with 200 grams of deionized water, and dissolved completely by heating. Under continuous heating condition, 378 grams (one mole) of hydrous crystalline trehalose was added to the solution, dissolved completely, and heated continuously. After boiling for about 30 minutes, the formation of crystals were observed. After stopping the heating and preserving the beaker at 60° C. for 24 hours, the content of the beaker formed a block comprising crystals and a sugar solution. After taking out the block from the beaker and crushing it roughly, crystals were collected after washing with spraying an appropriate amount of water using a bucket-type centrifugal separator. The collected crystals were dried in vacuo at 40° C. for four hours and then dried well by preserving in a desiccator containing phosphorous pentoxide at room temperature for 20 hours. As a result, about 400 grams of a white crystalline powder was obtained.

Experiment 1-1(b)

Figure 2:
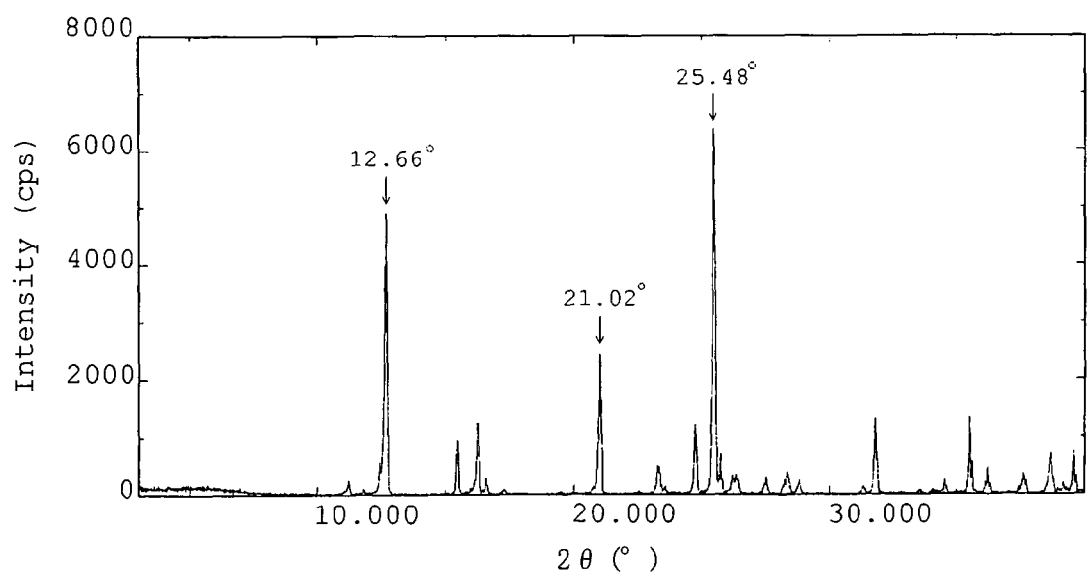
FIG. 2 shows an X-ray diffraction pattern of a crystalline associate of trehalose and calcium chloride (molar ratio of 1:2).
Figure 3:
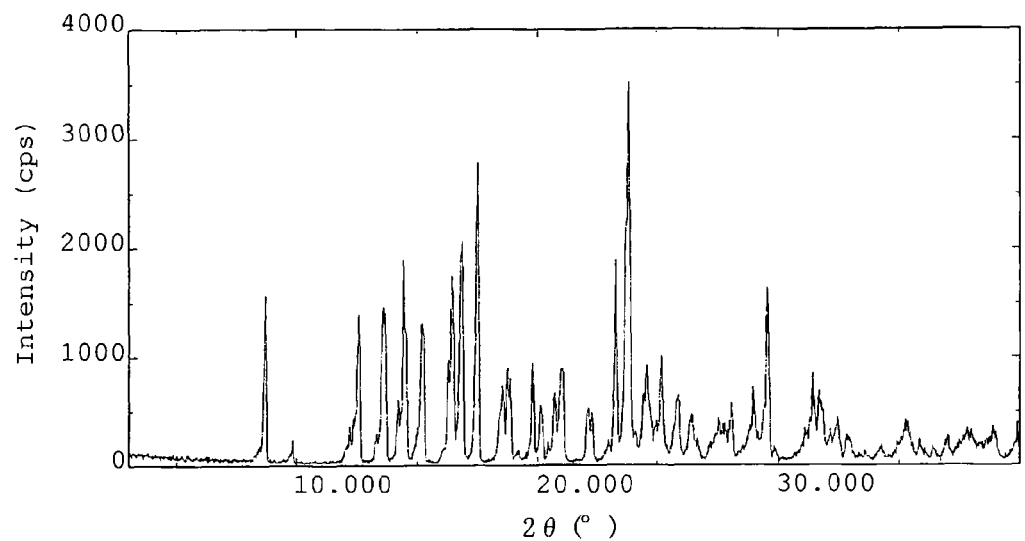
FIG. 3 shows an X-ray diffraction pattern of a hydrous crystalline trehalose.
Figure 4:
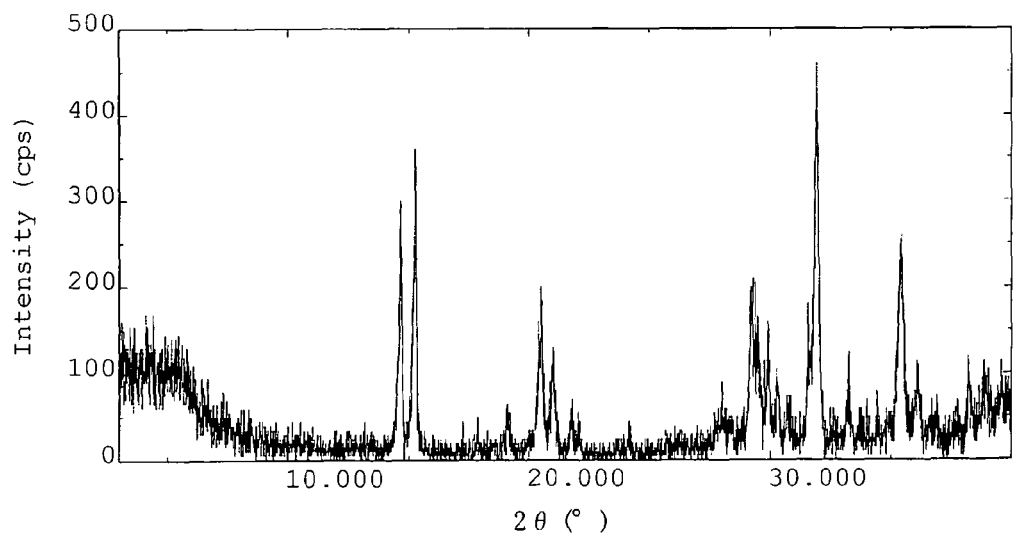
FIG. 4 shows an X-ray diffraction pattern of a crystalline calcium chloride dihydrate.

Physicochemical Properties of Crystalline Associate (1) X-Ray Diffraction Analysis Two kinds of crystals, obtained by the two different methods described in Experiment 1-1(a), were respectively analyzed for X-ray diffraction pattern on conventional powdery X-ray diffraction analysis using an X-ray diffractometer, "RAD-2B", commercialized by Rigaku Corporation, Tokyo, Japan. Also, X-ray diffraction patterns of hydrous crystalline trehalose and calcium chloride dihydrate were analyzed with the same method. X-Ray diffraction pattern of a crystal obtained from a mixture of trehalose and calcium chloride with a molar ratio of 1:1, that was obtained from a mixture of trehalose and calcium chloride with a molar ratio of 1:2, hydrous crystalline trehalose, and calcium chloride dihydrate, all of which were obtained in Experiment 1-1(a), were shown in FIGS. 1 to 4, respectively. As is evident from the results of FIGS. 1 to 4, X-ray diffraction pattern of FIG. 1 shows a main characteristic diffraction angle (2θ) of 9.02° and other angles of 17.98° and 21.90°, whereas the X-ray diffraction pattern of FIG. 2 shows main diffraction angles of 12.66°, 21.02°, and 25.48°. The both diffraction patterns were quite different from those of hydrous crystalline trehalose (FIG. 3) and calcium chloride (FIG. 4). These results mean that two kinds of crystals obtained in Experiment 1-1(a) are not a mixture of crystals of hydrous crystalline trehalose and calcium chloride dehydrate, and the crystals are quite different from crystals having independent crystal structures.

(2) Component Analysis

Each crystal, obtained by the two different methods, was analyzed for components as follows:

Trehalose

Twenty-five milligrams of each of the above crystal was dissolved in 5 ml of pyridine containing 2 mg/ml of phenyl-β-D-glucoside as an internal standard for gas chromatography. After converting the saccharide in 250 μl portion of each solution into a trimethylsiliy-derivative by conventional method, the sample was analyzed on gas chromatography (a column, "OV-17, commercialized by GL Sciences, Inc., Tokyo, Japan). Separately, hydrous crystalline trehalose as a standard was weighed accurately and analyzed by gas chromatography. The amount of trehalose per one gram of the crystal in each sample was calculated based on the peak areas of the sample and the standard.

Calcium

Twenty-five milligrams each of the above crystal was dissolved in 1% (v/v) of hydrochloric acid, and the resulting solution was diluted to 100-fold with 10% (w/v) of lanthanum chloride solution. Then, calcium content of each diluted solution was measured using an atomic absorption photometry ("model 5100" commercialized by Perkin-Elmer Japan Co., Ltd., Yokohama, Japan). The amount of calcium chloride per one gram of crystal was calculated from the value on the basis of the hypothesis that all calcium comprised in crystal is a form of calcium chloride.

Moisture

The amount of moisture per one gram of each of the above crystal was measured by conventional loss-on-drying method using five grams of the crystal.

The results obtained from the above analyses are summarized in Table 1.

TABLE 1

| Crystal* | Amount (mg)/g-crystal | | | Molar ratio in crystal | | |
|---|---|---|---|---|---|---|
| | Trehalose | CaCl$_2$** | Moisture | Trehalose | CaCl$_2$ | Moisture |
| 1:1 | 704.6 | 276.7 | 48.0 | 1 | 1.21 | 1.29 |
| 1:2 | 604.5 | 399.0 | 0.0 | 1 | 2.03 | 0.00 |

*Denotations of "1:1" and "1:2" mean crystals obtained from solutions having molar ratios of trehalose and calcium chloride of 1:1 and 1:2, respectively.
**Amount of calcium chloride per 1 gram of crystal calculated based on the hypothesis that all calcium detected by atomic absorption photometry is calcium chloride.

From the results described in Table 1, it was revealed that the first crystal, obtained in Experiment 1-1(a), contained trehalose, calcium chloride, and water as constituents, in the form of crystalline monohydrate of an associate having the above constituents in a molar ratio of 1:1:1, and that the second crystal contained trehalose and calcium chloride as constituents in the form of anhydrous crystal of an associate having the above constituents in a molar ratio of 1:2. Hereinafter, the first and second crystals obtained in Experiment 1-1(a) are called "associate of trehalose and calcium chloride (molar ratio of 1:1)" and "associate of trehalose and calcium chloride (molar ratio of 1:2), respectively.

Experiment 1-2

NMR Analysis of Associate Formed from Trehalose and Calcium Chloride

In order to analyze the mechanism of association of trehalose and calcium chloride in two kinds of associates of trehalose and calcium chloride (molar ratios of 1:1 and 1:2), the following NMR analyses were carried out:

(1) $^{13}$C-NMR

Fifty milligrams of two kinds of associate crystals of trehalose and calcium chloride (molar ratios of 1:1 and 1:2) and hydrous crystalline trehalose were dissolved in one milliliter of 99.9% deuterium oxide and analyzed on $^{13}$C-NMR as follows. NMR analysis was done using an instrument, "model JNM-AL300", commercialized by JOEL Ltd., Tokyo, Japan, a nucleus measurement of $^{13}$C, and resonance frequency of 75.45 MHz. After setting a tube containing the above solution to the instrument, spin-lattice relaxation time (herein after, called simply "relaxation time") of individual carbon atoms of trehalose in the solution was measured according to the inversion recovery method described in the operation manual attached to the instrument. Individual peak (chemical shift, ppm), obtained as the result of analysis, was assigned based on the data described by J. H. Bradbery et al. in *Carbohydrate Research*, Vol. 126, 125-126, (1984). Assignments of carbon atoms and their relaxation times are in Table 2. (The result of trehalose only, associate of trehalose and calcium chloride (molar ration of 1:1), and that (molar ratio of 1:2 are in Table 2-1, 2-2, and 2-3, respectively.)

TABLE 2

| Assignment (Carbon atom No.) | Chemical Shift (ppm) | Relaxation Time (msec) | (%)* |
|---|---|---|---|
| 1. Trehalose | | | |
| 1 | 96.847 | 408 | |
| 2 | 75.148 | 443 | |
| 3 | 74.752 | 427 | |
| 4 | 73.656 | 456 | |
| 5 | 72.321 | 499 | |
| 6 | 63.181 | 271 | |
| 2. Associate of trehalose and calcium chloride (molar ratio of 1:1) | | | |
| 1 | 95.851 | 362 | 89 |
| 2 | 75.156 | 408 | 92 |
| 3 | 74.768 | 342 | 80 |
| 4 | 73.664 | 415 | 91 |
| 5 | 72.329 | 384 | 77 |
| 6 | 63.181 | 252 | 93 |
| 3. Associate of trehalose and calcium chloride (molar ratio of 1:2) | | | |
| 1 | 95.818 | 375 | 92 |
| 2 | 75.123 | 404 | 91 |
| 3 | 74.735 | 385 | 90 |
| 4 | 73.631 | 466 | 102 |
| 5 | 72.324 | 360 | 72 |
| 6 | 63.164 | 249 | 92 |

*Relative relaxation time, when the corresponding relaxation time of trehalose is regarded as 100%. Bold letter means that the relaxation time of the carbon atom reduced remarkably by the association.

As shown in Table 2, the relaxation time of carbon atom(s) at C2 and/or C4 position(s) was remarkably reduced in two kinds of associates of trehalose and calcium chloride (molar ratios of 1:1 and 1:2). Therefore, it was suggested that the direct interaction between hydroxyl group bound to carbon atom(s) at C2 and/or C4 position(s) and calcium chloride involved the association of trehalose and calcium chloride.

(2) $^1$H-NMR

Fifty milligrams of two kinds of associate crystals of trehalose and calcium chloride (molar ratios of 1:1 and 1:2) and hydrous crystalline trehalose were dissolved in one milliliter of dimethylsulfoxide-d4 and analyzed on $^1$H-NMR as follows. NMR analysis was done using an instrument, "model JNM-AL300", commercialized by JOEL Ltd., Tokyo, Japan, a nucleus measurement of $^1$H, a resonance frequency of 300.4 MHz, and eight-integration times. Individual peak (chemical shift, ppm), obtained as the result of analysis, was assigned according to the two-dimensional NMR method described in "*Jikken-Kagaku-Kohza* 5 (Course of Experimental Chemistry)", pp. 302-312, edited by The Chemical Society of Japan, published by Maruzen Co., Ltd.; (1991), with referring the results of $^{13}$C-NMR in Table 2. The chemical shifts of protons of trehalose, assigned to the respective position in trehalose molecule by the analysis, were compared with those of associates of trehalose and calcium chloride (molar ratios of 1:1 and 1:2). Chemical shifts of protons, showing a remarkable difference between trehalose and associates, are summarized in Table 3.

TABLE 3

| | Chemical Shift (ppm) | | |
|---|---|---|---|
| Assignment* | Tre** | Tre-CaCl$_2$ (1:1)** | Tre-CaCl$_2$ (1:2)** |
| OH-2 or OH-4 | 4.808 | 4.932 | 4.850 |
| | 4.804 | 4.915 | 4.833 |
| | 4.791 | 4.887 | 4.827 |
| | 4.791 | 4.875 | 4.811 |
| OH-3 | 4.645 | 4.724 | 4.657 |
| | 4.624 | 4.705 | 4.637 |

TABLE 3-continued

| Assignment* | Chemical Shift (ppm) | | |
|---|---|---|---|
| | Tre** | Tre-CaCl$_2$ (1:1)** | Tre-CaCl$_2$ (1:2)** |
| OH-6 | 4.419 | 4.498 | 4.430 |
| | 4.400 | 4.478 | 4.410 |
| | 4.381 | 4.459 | 4.391 |

*The position of hydroxyl group is represented by using its bound carbon atom number.
**Denotations of "Tre", "Tre-CaCl$_2$(1:1)", and "Tre-CaCl$_2$(1:2)" mean trehalose, an associate of trehalose and calcium chloride (molar ratio of 1:1), and an associate of trehalose and calcium chloride (molar ratio of 1:2), respectively.

As shown in Table 3, the chemical shifts of all hydroxyl protons of trehalose were remarkably changed when trehalose associated with calcium chloride in comparison with those of intact trehalose. This result directly evidences that trehalose and calcium chloride form an associate by interacting hydroxyl protons of trehalose with calcium chloride. In consideration of the above result of $^{13}$C-NMR analysis, it was suggested that interaction of hydroxyl proton(s) bound to carbon atom(s) at C2 and/or C4 position(s) and calcium chloride were involved considerably in the formation of two kinds of associates of trehalose and calcium chloride (molar ratios of 1:1 and 1:2).

Experiment 2

Associates Formed from Trehalose and Other Metal Ion Compounds or Bittern Components Experiment 2-1

NMR Analysis of Associate Formed from Trehalose and Magnesium Chloride, Strontium Chloride, or Bittern Components A mixture, composed of 20.3 grams of magnesium chloride hexahydrate and 37.8 grams of hydrous crystalline trehalose (molar ratio 1:1), was admixed with 20 grams of deionized water and dissolved completely by heating. Similarly, a mixture, composed of 26.6 grams of strontium chloride hexahydrate and 37.8 grams of hydrous crystalline trehalose (molar ratio 1:1), was admixed with 20 grams of deionized water and dissolved completely by heating. After cooling to ambient temperature, these solutions were dried in vacuo at 80° C. for 15 hours. The resulting dried materials were pulverized conventionally to produce two kinds of powder.

Twenty milliliters (containing 6.42 grams of dry solid) of a commercially available bittern components, commercialized by Sanuki Engyou Co., Ltd., Kagawa, Japan, was admixed with 10 grams of hydrous crystalline trehalose and dissolved completely by heating. The solution was dried in vacuo at 80° C. for 15 hours and the resulting dried material was pulverized conventionally to produce a powder.

(1) $^{13}$C-NMR

According to the method described in Experiment 1-2, 50 mg of either of the above three kinds of powders were respectively dissolved in one ml of deuterium oxide, and the relaxation times of each carbon atoms of trehalose were analyzed on $^{13}$C-NMR. The relative values of the relaxation times of each carbon atoms, thus obtained, to those obtained from trehalose only were calculated based on the results of hydrous crystalline trehlose obtained in Experiment 1-2 in Table 2-1. The results are summarized in Table 4.

TABLE 4

| Assignment (Carbon atom No.) | Chemical Shift (ppm) | Relaxation Time (msec) | (%)* |
|---|---|---|---|
| 1. Associate of trehalose and magnesium chloride | | | |
| 1 | 95.917 | 392.3 | 96 |
| 2 | 75.213 | 462.3 | 104 |
| 3 | 74.843 | 392.0 | 92 |
| 4 | 73.730 | 467.8 | 103 |
| 5 | 72.395 | 418.6 | 84 |
| 6 | 63.230 | 274.6 | 101 |
| 2. Associate of trehalose and strontium chloride | | | |
| 1 | 95.834 | 377.4 | 93 |
| 2 | 75.139 | 422.3 | 95 |
| 3 | 74.760 | 345.5 | 81 |
| 4 | 73.648 | 415.7 | 91 |
| 5 | 72.312 | 398.3 | 80 |
| 6 | 63.172 | 288.6 | 107 |
| 3. Associate of trehalose and bittern components | | | |
| 1 | 95.886 | 406.8 | 100 |
| 2 | 75.183 | 484.8 | 109 |
| 3 | 74.813 | 410.5 | 96 |
| 4 | 73.700 | 486.1 | 107 |
| 5 | 72.365 | 424.4 | 85 |
| 6 | 63.200 | 273.6 | 101 |

*Relative relaxation time, when the corresponding relaxation time of trehalose is regarded as 100%. Bold letter means that the relaxation time of the carbon atom decreased remarkably by the association.

As is evident from the results in Table 4, all the powders, obtained from the mixture of trehalose and magnesium chloride, that of trehalose and strontium chloride, and that of trehalose and bittern components by dissolving and drying in vacuo, showed a remarkably reduced relaxation time of carbon atom at a specific position in comparison with the case of trehalose only. From the results, it was revealed that trehalose formed an associate with magnesium chloride, strontium chloride, and bittern components by direct interaction as in the case of calcium chloride, i.e., the above three kinds of powders were respectively associates of trehalose and magnesium chloride, trehalose and strontium chloride, and of trehalose and bittern components. Further, from the results in Tables 4-1, 4-2, and 4-3, it was supposed that the interaction of hydroxyl group(s) bound to carbon atom(s) at C-2 and/or C-4 position(s) of trehalose and metal ion compounds was involved deeply in the formation of associate of trehalose and magnesium chloride, trehalose and strontium chloride, and of trehalose and bittern components.

(2) $^1$H-NMR

According to the method in Experiment 1-2, 50 mg of either of the above three kinds of powders were respectively dissolved in one ml of dimethylsulfoxide-d4 and analyzed on $^1$H-NMR. The proton peaks (chemical shifts, ppm) of trehalose, observed by $^1$H-NMR, were assigned. The results are in Table 5.

As in the case of the associates of trehalose and calcium chloride, the chemical shifts of hydroxyl-proton of associates of trehalose and metal ion compounds were remarkably different from those of trehalose only. The chemical shifts of these protons are in Table 5 along with those of trehalose only shown in Table 3.

TABLE 5

| Assignment *1 | Chemical Shift (ppm) | | | |
|---|---|---|---|---|
| | Tre *2 | Tre-MgCl$_2$ *2 | Tre-SrCl$_2$ *2 | Tre-bittern components *2 |
| OH-2 or OH-4 | 4.808 | 4.985 | 4.932*3 | 4.985 |
| | 4.804 | 4.970 | | 4.970 |
| | 4.791 | 4.867 | | 4.867 |
| | 4.791 | 4.761 | | 4.761 |
| OH-3 | 4.645 | 4.661 | 4.738 | 4.661 |
| | 4.624 | 4.643 | 4.720 | 4.643 |
| OH-6 | 4.419 | 4.514 | 4.487*3 | 4.514 |
| | 4.400 | 4.495 | | 4.495 |
| | 4.381 | 4.475 | | 4.475 |

*1 The position of hydroxyl group is represented by using its carbon atom number bound.
*2 The denotations of "Tre", "Tre-MgCl$_2$", "Tre-SrCl$_2$" and "Tre-bittern components" mean trehalose, an associate of trehalose and magnesium chloride, an associate of trehalose and strontium chloride, and a powdery product comprising an associate of trehalose and bittern components, respectively.
*3 Large letter means that plural peaks (signals) observed in the case of trehalose were flocked in one position.

As shown in Table 5, all the chemical shifts of hydroxyl-protons of trehalose remarkably changed when associates were formed from trehalose and magnesium chloride, strontium chloride, or bittern components in comparison with the case of trehalose only. The results directly evidence that trehalose also formed associates with magnesium chloride, strontium chloride, and bittern components. Taking account of the above results of $^{13}$C-NMR analyses, it was supposed that the interaction of hydroxyl proton(s) bound to carbon atom(s) at C-2 and/or C-4 position(s) of trehalose and metal ion compounds was specially involved deeply in the formation of above associates of trehalose and metal ion compounds.

Experiment 2-2

Change of Solubility of Metal Ion Compounds by the Association with Trehalose

The changes of solubility in water of trehalose and/or metal ion compounds were examined under coexistence of trehalose and metal ion compounds. Hydrous crystalline trehalose was used for the tests. Strontium chloride hexahydrate, cuprous chloride dihydrate, ferrous chloride tetrahydrate, manganese chloride tetrahydrate, and nickel chloride hexahydrate were used as metal ion compounds for the tests. 37.8 grams of hydrous crystalline trehalose (0.1 mole) and 0.1 mole of either of the above metal ion compounds was placed in a 100 ml-glass beaker and admixed with deionized water to give 30 grams of water per beaker with taking account of bound water of trehalose and metal ion compounds, and then the contents in the beaker were dissolved by heating. Solutions prepared by dissolving the same amount of trehalose only or that of metal ion compounds only were prepared as controls. After dissolving the contents completely, all the beakers were allowed to stand at room temperature (25° C.) for 24 hours. Successively, precipitation of crystals was judged by macroscopic observation. In the case of precipitating crystals, the formed crystals were collected and analyzed for those component(s) by conventional method. The results are in Table 6.

TABLE 6

| | Precipitation of crystal | |
|---|---|---|
| Metal ion compound | In the presence of trehalose | In the absence of trehalose |
| Strontium chloride | Crystalline strontium chloride was slightly precipitated. | Precipitated (strontium chloride) |
| Cuprous chloride | Crystalline cuprous chloride was slightly precipitated. | Precipitated (cuprous chloride) |
| Ferrous chloride | Crystalline ferrous chloride was slightly precipitated. | Precipitated (ferrous chloride) |
| Manganese chloride | None | Precipitated (manganese chloride) |
| Nickel chloride | None | Precipitated (nickel chloride) |
| None (Control) | Crystalline trehalose was precipitated | — |

Referring to the case of strontium chloride, which was confirmed to form an associate with trehalose by NMR analysis (Experiment 2-1), crystals of strontium chloride were clearly observed in the absence of trehalose. However, the amount of crystals was remarkably decreased in the presence of trehalose. The result indicates that the associations of metal ion compounds and trehalose can be judged by investigating the change of solubility in water of the metal ion compounds in the presence of trehalose. Referring to the results of cuprous chloride, ferrous chloride, manganese chloride, and nickel chloride (Table 6, the row of cuprous chloride through the row of nickel chloride), the solubility in water of these metal ion compounds were remarkably improved in the presence of trehalose. Accordingly, based on the above judgement, it was revealed that these metal ion compounds also formed associates with trehalose in the presence of trehalose. Compared with the result of control (Table 6, the lowest row), not containing metal ion compound, trehalose was precipitated from a solution containing trehalose only under the present experimental condition, while trehalose was not precipitated in the presence of the above metal ion compounds. Form the result, it was revealed that trehalose as well as the metal ion compounds used in the present experiment were improved in their inherent solubilities in water by associating.

Experiment 3

Associate of Maltitol and Metal Ion Compound

A mixture of 100 mg, d.s.b., of maltitol and 85.3 mg, d.s.b., of calcium chloride was dissolved in one milliliter of deuterium oxide. The solution was analyzed according to the $^{13}$C-NMR described in Experiment 1-2 and the relaxation time of each carbon atom of maltitol was analyzed. Individual peak (chemical shift, ppm), observed in this analysis, was assigned based on the data described by J. H. Bradbery et al. in *Carbohydrate Research*, vol. 126, 125-126(1984). The solution prepared with 100 mg, d.s.b., of maltitol only was similarly analyzed as a control. The results are summarized in Table 7.

TABLE 7

| Assignment (Carbon atom No.) | Chemical Shift (ppm) | Relaxation Time (msec) | |
|---|---|---|---|
| 1. Maltitol | | | |
| Glucosyl residue | | | |
| 1 | 102.815 | 401 | |
| 2 | 75.115 | 415 | |
| 3 | 75.453 | 470 | |
| 4 | 71.868 | 457 | |
| 5 | 75.371 | 467 | |
| 6 | 63.000 | 249 | |
| Sorbitol residue | | | |
| 1' | 65.481 | 364 | |
| 2' | 74.275 | 472 | |
| 3' | 75.527 | 464 | |
| 4' | 83.909 | 441 | |
| 5' | 74.077 | 455 | |
| 6' | 64.846 | 337 | |

| Assignment (Carbon atom No.) | Chemical Shift (ppm) | Relaxation Time (msec) | (%)* |
|---|---|---|---|
| 2. Associate of maltitol and calcium chloride | | | |
| Glucosyl residue | | | |
| 1 | 103.128 | 358 | 89 |
| 2 | 75.073 | 401 | 96 |
| 3 | 75.483 | 421 | 90 |
| 4 | 71.991 | 380 | 83 |
| 5 | 75.263 | 410 | 88 |
| 6 | 63.016 | 237 | 95 |
| Sorbitol residue | | | |
| 1' | 65.422 | 297 | 82 |
| 2' | 74.224 | 389 | 82 |
| 3' | 73.079 | 329 | 72 |
| 4' | 84.452 | 378 | 86 |
| 5' | 74.134 | 327 | 72 |
| 6' | 64.911 | 297 | 88 |

*Relative relaxation time, when the corresponding relaxation time of maltitol is regarded as 100%. Bold letter means that the relaxation time of the carbon atom decreased remarkably by the association.

As shown in Table 7, in the mixture solution of maltitol and calcium chloride, the relaxation times of carbon atoms at C-4 position of glucose residue and at C-3' and C-5' positions of sorbitol residue were remarkably reduced in comparison with the case of maltitol only. From the results, it was revealed that maltitol formed an associate with calcium chloride by the direct interaction. Further, from the results described above, it was supposed that the direct interaction of hydroxyl groups, bound to carbon atoms at C-4 position of glucose residue and at C-3' and C-5' positions of sorbitol residue, and calcium chloride were mainly involved deeply in the formation of an associate of maltitol and metal ion compounds.

Experiment 4

Hygroscopicity of Associate of Trehalose and Calcium Chloride or bittern Components In order to compare the hygroscopicity (deliquescent property) of a powder, comprising an associate of trehalose and calcium chloride or that of trehalose and bittern components, with a control, a dried powder of calcium chloride or bittern components, which is known to have a high deliquescent property, the following hygroscopicity test was carried out. Two kinds of crystalline associates of trehalose and calcium chloride (molar ratios of 1:1 and 1:2) prepared according to the method described in Experiment 1-1 or 1-2, powders comprising associates of trehalose and bittern components, calcium chloride dihydrate, or a dried bittern components powder were used as test samples. A dried bittern powder was prepared by drying bittern solution in vacuo at 60° C. for 15 hours, pulverized, and dried in a usual manner for use as a control. The moisture content (weight of moisture per one gram of the sample) of each sample was measured by conventional drying loss method. The moisture content of an associate of trehalose and calcium chloride (molar ratio 1:1), an associate of trehalose and calcium chloride (molar ratio 1:2), a powder comprising an associate of trehalose and bittern components, calcium chloride dihydrate, and a dried bittern powder were 0.048 g, 0.000 g, 0.061 g, 0.245 g, and 0.214 g, respectively. These samples, about 1.5 g each, were respectively placed in an aluminum cup and preserved at 25° C. for seven days in a desiccator which was controlled to keep at a relative humidity of 33.0% or 52.8%. The weight of the content in each cup was measured at the initiation of preservation (0 day preservation), and 1, 2, 4, and 7 days after the initiation. The amount of moisture per one gram of each at sample after 1 to 7 days preservation was calculated based on the assumption that the increased amount measured to that of 0 day preservation was the amount of moisture absorbed by each sample. The results are in Table 8.

TABLE 8

| Relative Humidity | Sample* | Moisture content/g-sample (g) | | | | |
|---|---|---|---|---|---|---|
| | | 0 day | 1 day | 2 days | 3 days | 7 days |
| 33.0% | $CaCl_2 \cdot 2H_2O$ | 0.245 | 0.289 | 0.312 | 0.343 | 0.364 |
| | Tre-$CaCl_2$ (1:1) | 0.048 | 0.048 | 0.048 | 0.048 | 0.048 |
| | Tre-$CaCl_2$ (1:2) | 0.000 | 0.010 | 0.010 | 0.011 | 0.011 |
| | DPBC** | 0.214 | 0.299 | 0.349 | 0.378 | 0.398 |
| | Tre-BC*** | 0.061 | 0.164 | 0.182 | 0.182 | 0.175 |
| 52.8% | $CaCl_2 \cdot 2H_2O$ | 0.245 | 0.319 | 0.359 | 0.405 | 0.430 |
| | Tre-$CaCl_2$ (1:1) | 0.048 | 0.054 | 0.059 | 0.059 | 0.060 |
| | Tre-$CaCl_2$ (1:2) | 0.000 | 0.016 | 0.017 | 0.018 | 0.021 |
| | DPBC** | 0.214 | 0.412 | 0.462 | 0.495 | 0.523 |
| | Tre-BC*** | 0.061 | 0.253 | 0.294 | 0.337 | 0.356 |

*Denotations of "$CaCl_2 \cdot 2H_2O$", "Tre-$CaCl_2$ (1:1)", "Tre-$CaCl_2$ (1:2)", and "Tre-BC" mean calcium chloride dihydrate, an associate of trehalose and calcium chloride (molar ratio of 1:1), an associate of trehalose and calcium chloride (molar ratio of 1:2), and a powdery product comprising an associate of trehalose and bittern components.
**Dried powdery bittern components.
***Bittern components.

As shown in Table 8, calcium chloride dihydrate began to absorb moisture from the beginning of the preservation under the above all relative humidity conditions. The moisture contents per one gram of each sample were reached 0.364 gram at a relative humidity of 33.0% and 0.430 gram at a relative humidity of 52.8% after seven-days preservation. On the other hand, two kinds of associates of trehalose and calcium chloride showed almost no absorption of moisture after seven-days preservation and almost no increase in the moisture contents. The degree of absorbing moisture of the samples were evidently low in comparison with the case of calcium chloride. Further, two kinds of associates of trehalose and calcium chloride showed no deliquescence at the macroscopic observation whereas calcium chloride showed that. The above results indicate that the inherent property for the deliquescence of calcium chloride is improved in the associates of trehalose and calcium chloride.

The dried bittern powder began to absorb moisture from the beginning of the preservation under the above all relative humidity conditions. The moisture contents per one gram of each sample were reached to high values of 0.398 gram at a relative humidity of 33.0% and 0.523 gram at a relative humidity of 52.8% after seven-days preservation. On the other hand, those of a powder comprising the associate of trehalose and bittern components reached 0.175 gram at a relative humidity of 33.0% and 0.356 gram at a relative humidity of 52.8% after seven-days preservation. The moisture contents of the samples were evidently low in comparison with the case of the dried bittern powder. Further, the powder comprising an associate of trehalose and bittern components showed no deliquescence at the macroscopic observation whereas the dried bittern powder showed that. The above results indicate that inherent property for the deliquescence of dried bittern powder is improved in the powder comprising an associates of trehalose and bittern components. The above property of the associates of trehalose and bittern components can be advantageously used for the production of dried-seafoods, i.e., dried-seaweeds such as dried kelp, dried brown seaweed, dried sealettuce, laver and the like; dried-whole fishes or dried-opened fishes such as flying fish, barracuda, sand borer, scad, mackerel, "hokke", sardine, saury, halfbeak, flounder, octopus, squid, and the like, whose higroscopicity are decreased, by the steps of contacting the seafoods with trehalose in an aqueous solvent, desirably, with a trehalose solution with a trehalose concentration of 2% (w/w) or higher, forming an associate of trehalose and bittern components contained in seafoods, and drying the mixture into dried seafoods such as seaweeds and fishes.

Experiment 5

Suppressing Effect of Trehalose and Maltitol on the Formation of Calcium Phosphate Precipitate When phosphate ion is added to a calcium chloride aqueous solution, calcium phosphate, an insoluble salt, is formed from calcium ion and phosphate ion and then precipitated. Effects of trehalose, maltitiol, and other saccharides on the phenomenon were investigated as follows. A calcium chloride aqueous solution was prepared by the steps of adding 3.68 grams of calcium chloride dihydrate to deionized water to dissolve therein and adding deionized water to the solution to give a total volume of 200 ml. Hydrous crystalline trehalose, anhydrous crystalline maltitol, hydrous crystalline maltose, and anhydrous crystalline sucrose were used as saccharides for testing. A phosphate solution (pH 6.8) was prepared by the steps of mixing 250 ml of 0.2 M potassium dihydrogen phosphate solution with 118 ml of 0.2 M sodium hydroxide solution, and filling up the resulting solution to one liter with deionized water.

Twenty-six grams, d.s.b., of either of the saccharides for testing was added to 5 ml of the above calcium chloride solution and dissolved by adding additional deionized water. The resulting aqueous solutions were filled up to give a total volume of 50 ml. A control solution was prepared by the steps of adding deionized water only to five ml of the above calcium chloride solution and filling up the resulting solution to give a total volume of 50 ml with deionized water. Successively, 40 ml of the above phosphate solution was mixed with 10 ml of calcium chloride solution. After stirring at 37° C. for three hours, each solution was centrifuged at 10,000 rpm for 10 minutes and the resulting supernatant was collected. The calcium concentration (the solubilized calcium concentration) of each supernatant was measured using "ZEEMAN 5100", an atomic adsorption-photometer commercialized by Perkin-Elmar Japan Co. Ltd., Kanagawa, Japan. Samples for measurement were prepared by the steps of adding two ml of 10% (w/v) lanthanum chloride solution to five ml of each of the above supernatants after centrifugation and filling up the resulting solution to give 25 ml with deionized water.

The above procedure was carried out for individual each sample (four kinds of saccharides and control) for three times and the average value of the solubilized calcium concentration was calculated. The results are summarized in Table 9.

TABLE 9

| Saccharide | Concentration of solubilized calcium (mg/l, average ± standard deviation) |
|---|---|
| None (Control) | 6.86 ± 0.49 |
| Trehalose | 23.90 ± 2.54 |
| Maltitol | 20.13 ± 1.17 |
| Maltose | 6.79 ± 0.52 |
| Sucrose | 6.54 ± 0.31 |

As shown in Table 9, It was revealed that trehalose and maltitol had an ability of suppressing the precipitation of calcium phosphate which is formed by the coexistence of calcium ion and phosphate ion. From the results in Experiments 1 to 3, showing trehalose and maltitol formed associates with metal ion compounds, it was considered that trehalose and maltitol inhibited the formation of insoluble salt (calcium phosphate), formed with ionic bond between calcium ion and phosphate ion, by associating with the solubilized calcium salt (calcium chloride in this experiment).

Experiment 6

Solubility-Improving Effect of Trehalose and Maltitol on Calcium-Organic Acid Salt Effects of trehalose, maltitol, and other saccharides on the solubilities of calcium-organic acid salts were investigated as follows. Three kinds of saccharide solutions comprising different sacchairde were prepared by dissolving 5 grams, d.s.b., of trehalose, maltitol and maltose in 35 ml of deionized water. Successively, five grams of commercially available calcium DL-lactate pentahydrate or calcium gluconate monohydrate, used as calcium-organic acid salts, were added to each saccharide solution, followed by suspension. Thereafter, the pH of each solution was adjusted to 3.5, and the solution was filled up to give a volume of 50 ml with deionized water. After stirring at 25° C. for 16 hours, insoluble calcium-organic acid salts were removed by centrifuging (15,000 rpm for 30 minutes). The pHs of the resulting supernatants were measured. The calcium concentrations of the supernatant were measured using an atomic adsorption photometer described in Experiment 5. The solution prepared with no saccharide was also measured for calcium concentration in the same manner as control. The results are in Table 10.

TABLE 10

| | Calcium lactate | | | Calcium gluconate | | |
|---|---|---|---|---|---|---|
| | pH | Ca conc. (mg/ml) | Relative conc. (%) | pH | Ca conc. (mg/ml) | Relative conc. (%) |
| None | 3.7 | 10.44 | 100 | 3.7 | 4.54 | 100 |
| Trehalose | 3.7 | 13.46 | 129 | 3.7 | 5.07 | 112 |
| Maltitol | 3.7 | 12.82 | 123 | 3.7 | 5.83 | 128 |
| Maltose | 3.7 | 10.19 | 98 | 3.7 | 4.73 | 104 |

As shown in Table 10, the pH of all supernatants was 3.7. The calcium concentrations in supernatants were increased by the addition of trehalose or maltitol. In the case of calcium lactate, calcium concentration in the supernatant was increased by 29% by trehalose and 23% by maltitol in comparison with that of control. In the case of calcium gluconate, the calcium concentration in the supernatant was increased by 12% by trehalose and 28% by maltitol in comparison with that of control. It was revealed that trehalose and maltitol had the function of improving the solubility of calcium organic acid salts such as calcium lactate and calcium gluconate. The function of trehalose and maltitol was useful to prevent the clouding of soft drinks comprising calcium-organic acid salts, sports drinks, and mineral-supplement drinks, which is caused during the preservation for a long period of time.

Experiment 7

Suppressing Effect of Trehalose and Maltitol on the Oxidation of Ferrous Ion

Generally, ferrous ion (divalent, $Fe^{2+}$) and ferric ion (trivalent, $Fe^{3+}$) are known as ions of iron element. Ferrous ion is easily oxidized with light or heat and converted to ferric ion. Effects of trehalose and maltitol on the phenomenon were investigated as follows. An aqueous solution, comprising ferrous chloride ($FeCl_2$) tetrahydrate corresponding to the amount of 1% (w/v) as ferrous ion, and comprising trehalose or maltitol corresponding to the amount of 5% (w/v), d.s.b., was prepared as a test solution. While, a solution, comprising ferrous chloride only with the same concentration to the test solution, was prepared as a control solution. After preparing the test and control solutions, small portions of which were sampled respectively, and the amount of ferrous ion was measured by the Nitroso-DMAP method described later. Successively, 10 ml each of the test and control solution was placed separately in a 20 ml-vial and sealed. After preserving these vials at 37° C. for four hours with irradiating a light of about 9,000 luxes, the amount of ferrous ion in each solution was measured by the Nitroso-DMAP method. Measurement by the Nitroso-DMAP method was carried out as follows. After diluting the test or control solution accurately by 100-fold, 0.5 ml of the dilute was placed in a 50 ml-volumetric flask. Successively, five ml of 0.2% (w/v) nitroso-dimethyl-aminophenol in 0.1 N hydrochloric acid solution and four ml of 3 N ammonium buffer (pH8.5) were added quickly to the dilute and filled up accurately to give a volume of 50 ml with deionized water. After the above procedure, the absorbance at 750 nm (within the visible light range) of the solution was measured. The standard solutions, prepared by diluting stepwise a ferrous chloride solution with known concentration, were used for the measurement in the same manner to obtain a standard curve for quantitative analysis. The amount of ferrous ion of the test or the control solution was determined with the standard curve. The results are in Table 11.

TABLE 11

| | Amount of $Fe^{2+}$ ion (mg/ml) | |
| --- | --- | --- |
| Saccharide | Before light-irradiation | After light-irradiation |
| Trehalose | 10.1 | 4.4 |
| Maltitol | 10.2 | 4.3 |
| None (Control) | 10.2 | 3.8 |

As shown in Table 11, in the test solution comprising trehalose or maltitol, ferrous ion remained in evidently large amount after light-irradiation in comparison with that for the control solution. Taking account of the results and those in Experiment 2-2, which showed the formation of an associate from trehalose and an iron salt, it is considered that the above suppressing effect by trehalose and maltitol is the result of forming associates of these saccharides and an iron salt.

Experiment 8

Suppressing Effect of Trehalose and Maltitol on the Deterioration of Ascorbic Acid Under the Presence of Metal Ion L-Ascorbic acid deteriorates rapidly by the oxidative degradation in the presence of iron and copper ions and causes the browning. The effects of trehalose and maltitol on the phenomenon were investigated as follows. Ten kinds of aqueous solutions having respective compositions described in Table 12 were prepared. Aqueous solutions of L-ascorbic acid alone or L-ascorbic acid and metal ion compounds were used as controls. The test solutions were prepared by adding trehalose or maltitol to the control solutions. Ten milliliters of each of these test and control solutions were placed into different 20 ml-vials and sealed. The vials were preserved at 50° C. The control and test solutions, containing ferrous chloride, and those containing ferric chloride or copper sulfate were preserved for 96 hours and 40 hours, respectively. After the preservation, the degree of coloring of each solution was measured. In the case of a control solution containing L-ascorbic acid alone, the degrees of coloring were measured at the preservation periods of 40 hours and 96 hours. The absorbance at 420 nm (within the visible light range) of each sample was measured as the degree of coloring. The results are shown in Table 12.

TABLE 12

| | | Degree of coloring (Abs.** at 420 nm) | |
| --- | --- | --- | --- |
| Composition of Solution* | Note | Preserved for 40 hrs | Preserved for 96 hrs |
| 14.8 mM AsA | Control | 0.021 | 0.166 |
| 14.8 mM AsA + 10 mM $CuSO_4$ | Control | 0.800 | — |
| 14.8 mM AsA + 10 mM $CuSO_4$ + 100 mM Tre | Test | 0.311 | — |
| 14.8 mM AsA + 10 mM $CuSO_4$ + 100 mM Mal | Test | 0.258 | — |
| 14.8 mM AsA + 10 mM $FeCl_3$ | Control | 0.529 | — |
| 14.8 mM AsA + 10 mM $FeCl_3$ + 100 mM Tre | Test | 0.226 | — |
| 14.8 mM AsA + 10 mM $FeCl_3$ + 100 mM Mal | Test | 0.198 | — |
| 14.8 mM AsA + 10 mM $FeCl_2$ | Control | — | 0.588 |
| 14.8 mM AsA + 10 mM $FeCl_2$ + 100 mM Tre | Test | — | 0.380 |
| 14.8 mM AsA + 10 mM $FeCl_2$ + 100 mM Mal | Test | — | 0.291 |

*Denotations of "AsA", "Tre", and "Mal" mean L-ascorbic acid, trehalose, and maltitol, respectively.
**Absorbance As shown in Table 12, the degree of coloring of the test solutions, containing trehalose or maltitol, were remarkably low in comparison with that of the control. Taking account of the results and those in Experiment 2-2, which showed the formation of an associate of trehalose and an iron salt or a copper salt, it is considered that the above suppressing effects by trehalose and maltitol are the results of forming associates of these saccharides and iron salts and a copper salt.

Experiment 9

Suppressing Effect of Trehalose on the Formation of Scum from Boiling Foods

Scum is formed by boiling meat only or meat with vegetables. When scum is formed in an excessive amount, it should be removed. The effect of trehalose on the above phenomenon was investigated as follows. Thirty grams of pork and 20 grams of spinach were added to 400 ml of water and then 2% (w/w) or 10% (w/w) of trehalose or 2% (w/w) of sucrose was admixed therewith. Successively, the mixture was heated, boiled for one minute, stopped heating, and then cooled to room temperature. After cooling, scum was retrieved by the steps of collecting with a "KIRIYAMA" filter, washing with 500 ml of deionized water, and drying at 40° C. for 18 hours. Scum prepared similarly without using saccharide was used as a control. Weight of scum and the amount of main components comprised in the scum were measured. The results were shown in Table 13.

TABLE 13

| Saccharide | Amount % (w/w) | Weight of scum (g) | RW* (%) | Fat (g) | Protein (g) | Ash (g) | Ca (mg) | Mg (mg) |
|---|---|---|---|---|---|---|---|---|
| Trehalose | 2 | 0.506 | 46 | 0.406 | 0.076 | 0.009 | 1.613 | 0.810 |
| | 10 | 0.315 | 29 | 0.244 | 0.048 | 0.005 | 1.593 | 0.156 |
| Sucrose | 2 | 1.060 | 97 | 0.871 | 0.170 | 0.013 | 1.672 | 2.475 |
| None | 0 | 1.091 | 100 | 0.899 | 0.166 | 0.012 | 1.326 | 2.550 |

*Relative weight (%)

As shown in Table 13, the weight of scum was decreased with increase the amount of trehalose. While, sucrose had no effect of decreasing the amount of scum. The amount of scum formed by using sucrose was almost the same level with control. From the results, it was revealed that trehalose had a property of suppressing the formation of scum. From the component analysis of scum, it is supposed that calcium ion and magnesium ion are involved deeply in the suppression of scum-formation by trehalose. It is also supposed that trehalose suppresses the formation of insoluble magnesium ion compounds, specifically, magnesium-fatty acid salts.

Experiment 10

Suppressing Effect of Trehalose and Maltitol on the Formation of Scum During the Cooking of Boiled Foods Effects of trehalose and maltitol on the formation of scum were compared with those of other saccharides as follows. After adding 30 grams each of pork to 400 ml solution comprising 10% (w/w) of either trehalose, maltitol, neotrehalose, sucrose, maltose, or glucose and soaking for 10 minutes, the solution was heated and boiled for five minutes. After stopping the heating and cooling to room temperature, the resulting scum was retrieved by the steps of collecting with a "KIRIYAMA" filter, washing with 500 ml of deionized water, and drying at 40° C. for 18 hours. Scum prepared similarly without using saccharide was used as a control. Weight of scum obtained and the amount of minerals (calcium, magnesium, sodium, and potassium) comprised in the scum were measured. The results are in Table 14.

TABLE 14

| | Weight of scum | | Calcium | | Magnesium | | Sodium | | Potassium | |
|---|---|---|---|---|---|---|---|---|---|---|
| | (g) | (%) | (mg) | (%) | (mg) | (%) | (mg) | (%) | (mg) | (%) |
| None | 2.252 | 100 | 0.177 | 100 | 0.056 | 100 | 0.247 | 100 | 0.023 | 100 |
| Trehalose | 0.579 | 26 | 0.048 | 41 | 0.011 | 20 | 0.182 | 74 | 0.017 | 74 |
| Maltitol | 0.802 | 36 | 0.030 | 26 | 0.029 | 52 | 0.183 | 74 | 0.015 | 65 |
| Neotrehalose | 1.942 | 86 | 0.090 | 77 | 0.042 | 75 | 0.237 | 96 | 0.024 | 104 |
| Sucrose | 1.718 | 76 | 0.113 | 97 | 0.052 | 93 | 0.299 | 121 | 0.025 | 109 |
| Maltose | 2.126 | 94 | 0.092 | 79 | 0.050 | 89 | 0.283 | 115 | 0.025 | 109 |
| Glucose | 2.171 | 96 | 0.118 | 101 | 0.048 | 86 | 0.263 | 106 | 0.019 | 83 |

As shown in Table 14, in the case of using trehalose or maltitiol, the weight of scum formed were decreased to the level of less than half of the case of control (no saccharide). While, neotrehalose, sucrose, maltose, and glucose had no effect of decreasing the amount of scum. The amount of scum formed by using those saccharides was almost the same level with control (no saccharide). From the analysis of minerals comprised in scum, it was revealed that calcium and magnesium were law in content. It is supposed that trehalose and maltitol suppress the formation of scum by suppressing the formation of insoluble calcium and magnesium ion compounds.

Experiment 11

Suppressing Effect of Trehalose on the Elution of Magnesium from Boiled Foods During the Cooking Respective filtrates obtained by removing scum in Experiment 10 were filled up to give a total volume of 500 ml with water and the amount of minerals (calcium, magnesium, sodium, and potassium) comprised in the filtrates were measured. The results are in Table 15. It is considered that total amounts of minerals eluted from 30 grams of pork can be calculated by summing up the values in Table 14 (the amount in scum) and those in Table 15 (the amount in filtrate). Therefore, the total amounts and relative values calculated using the values of control (no saccharide) as having 100 parts are in Table 16.

TABLE 15

| | Ca | | Mg | | Na | | K | |
|---|---|---|---|---|---|---|---|---|
| | (mg) | (%) | (mg) | (%) | (mg) | (%) | (mg) | (%) |
| None | 0.964 | 100 | 1.158 | 100 | 3.442 | 100 | 6.325 | 100 |
| Trehalose | 0.788 | 82 | 0.485 | 42 | 3.490 | 101 | 6.035 | 95 |
| Maltitol | 1.425 | 148 | 1.523 | 132 | 3.412 | 99 | 6.150 | 97 |
| Neotrehalose | 0.957 | 99 | 1.148 | 99 | 3.880 | 113 | 6.060 | 96 |
| Sucrose | 0.977 | 101 | 1.150 | 99 | 3.420 | 99 | 6.165 | 97 |

TABLE 15-continued

|  | Ca | | Mg | | Na | | K | |
| --- | --- | --- | --- | --- | --- | --- | --- | --- |
|  | (mg) | (%) | (mg) | (%) | (mg) | (%) | (mg) | (%) |
| Maltose | 0.942 | 98 | 1.152 | 99 | 3.437 | 100 | 6.160 | 97 |
| Glucose | 1.051 | 109 | 1.149 | 99 | 3.426 | 100 | 6.285 | 99 |

TABLE 16

|  | Ca | | Mg | | Na | | K | |
| --- | --- | --- | --- | --- | --- | --- | --- | --- |
|  | (mg) | (%) | (mg) | (%) | (mg) | (%) | (mg) | (%) |
| None | 1.081 | 100 | 1.214 | 100 | 3.689 | 100 | 6.348 | 100 |
| Trehalose | 0.836 | 77 | 0.496 | 41 | 3.672 | 100 | 6.052 | 95 |
| Maltitol | 1.455 | 135 | 1.552 | 128 | 3.595 | 97 | 6.165 | 97 |
| Neotrehalose | 1.047 | 97 | 1.190 | 98 | 4.117 | 112 | 6.084 | 96 |
| Sucrose | 1.090 | 101 | 1.202 | 99 | 3.719 | 101 | 6.190 | 98 |
| Maltose | 1.034 | 96 | 1.202 | 99 | 3.720 | 101 | 6.185 | 97 |
| Glucose | 1.169 | 108 | 1.197 | 99 | 3.689 | 100 | 6.304 | 99 |

As shown in Table 16, in the case of saccharides except for trehalose and maltitol, the total amounts of respective minerals eluted from pork were almost the same as in the case of control (no saccharide). While, in the case of trehalose, especially, the amount of magnesium was less than half of the control and trehalose suppressed the elution of magnesium ion compounds. On the other hand, in the case of maltitol, the amounts of calcium and magnesium, eluted from pork, were larger than control, and maltitol promoted the elution of calcium and magnesium ion compounds from pork. From the results, it is supposed that maltitol suppresses the formation of scum by suppressing the insolubilization of calcium and magnesium ion compounds even though maltitol promotes the elution of those from pork. It is also supposed that trehalose suppresses the formation of scum by suppressing the elution of calcium and magnesium ion compounds, specifically, magnesium ion compounds from pork.

Experiment 12

Suppressing Effect of Trehalose on the Elution of Magnesium from Boiled Vegetables During the Cooking Suppressing effect of trehalose on the elution of magnesium was investigated on vegetables. After adding 20 grams of "shungiku" (garland chrysanthemum) or spinach to 400 ml of an aqueous solution comprising 10% (w/w) of trehalose and soaking for 10 minutes, the solution was heated and boiled for five minutes. After stopping the heating and cooling to room temperature, the resulting scum was retrieved by the steps of collecting with a "KIRIYAMA" filter, washing the collected scum with 500 ml of deionized water, and drying at 40° C. for 18 hours. The weight of scum and the amount of minerals comprised in the scum were measured with the same manner in Experiment 9. Filtrates obtained by removing scum were filled up to give a total volume of 500 ml with water and the amounts of minerals (calcium, magnesium, sodium, and potassium) were measured with the same manner in Experiment 10. Samples prepared with no saccharide and those prepared using sucrose instead of trehalose were used as control 1 and 2, respectively. Total amounts of minerals comprised in scum and filtrate were defined as the amount of minerals eluted from vegetables during the cooking. The amounts of minerals comprised in scum and filtrates are in Table 17 and 18, respectively. The sums of these (total amount of minerals eluted) are in Table 19.

TABLE 17

| Vegetable | Saccharide | Weight of scum | | Calcium | | Magnesium | | Sodium | | Potassium | |
| --- | --- | --- | --- | --- | --- | --- | --- | --- | --- | --- | --- |
|  |  | (g) | (%) | (μg) | (%) | (μg) | (%) | (μg) | (%) | (μg) | (%) |
| Garland | None | 0.014 | 100 | 0.410 | 100 | 0.092 | 100 | 0.197 | 100 | 0.380 | 100 |
| chrysanthemum | Trehalose | 0.008 | 57 | 0.156 | 38 | 0.034 | 37 | 0.074 | 37 | 0.300 | 79 |
|  | Sucrose | 0.010 | 71 | 0.299 | 73 | 0.059 | 63 | 0.058 | 29 | 0.288 | 76 |
| Spinach | None | 0.034 | 100 | 1.140 | 100 | 0.823 | 100 | 0.830 | 100 | 1.204 | 100 |
|  | Trehalose | 0.022 | 65 | 0.553 | 48 | 0.501 | 61 | 0.727 | 88 | 0.804 | 67 |
|  | Sucrose | 0.022 | 65 | 0.886 | 78 | 0.542 | 64 | 0.461 | 56 | 0.726 | 60 |

TABLE 18

| Vegetable | Saccharide | Calcium | | Magnesium | | Sodium | | Potassium | |
| --- | --- | --- | --- | --- | --- | --- | --- | --- | --- |
|  |  | (mg) | (%) | (mg) | (%) | (mg) | (%) | (mg) | (%) |
| Garland | None | 13.109 | 100 | 1.299 | 100 | 3.231 | 100 | 0.707 | 100 |
| chrysanthemum | Trehalose | 11.928 | 91 | 0.628 | 48 | 3.314 | 103 | 0.615 | 87 |
|  | Sucrose | 12.683 | 97 | 1.440 | 111 | 3.213 | 99 | 0.655 | 93 |
| Spinach | None | 4.426 | 100 | 6.986 | 100 | 1.954 | 100 | 0.778 | 100 |
|  | Trehalose | 3.850 | 87 | 3.264 | 47 | 1.879 | 96 | 0.752 | 97 |
|  | Sucrose | 4.604 | 104 | 6.954 | 100 | 1.918 | 98 | 0.825 | 106 |

TABLE 19

| Vegetable | Saccharide | Calcium | | Magnesium | | Sodium | | Potassium | |
| --- | --- | --- | --- | --- | --- | --- | --- | --- | --- |
|  |  | (mg) | (%) | (mg) | (%) | (mg) | (%) | (mg) | (%) |
| Garland | None | 13.109 | 100 | 1.299 | 100 | 3.231 | 100 | 0.707 | 100 |
| chrysanthemum | Trehalose | 11.928 | 91 | 0.628 | 48 | 3.314 | 103 | 0.615 | 87 |

TABLE 19-continued

| Vegetable | Saccharide | Calcium (mg) | Calcium (%) | Magnesium (mg) | Magnesium (%) | Sodium (mg) | Sodium (%) | Potassium (mg) | Potassium (%) |
|---|---|---|---|---|---|---|---|---|---|
| | Sucrose | 12.683 | 97 | 1.440 | 111 | 3.213 | 99 | 0.656 | 93 |
| Spinach | None | 4.427 | 100 | 6.987 | 100 | 1.955 | 100 | 0.779 | 100 |
| | Trehalose | 3.851 | 87 | 3.265 | 47 | 1.879 | 96 | 0.753 | 97 |
| | Sucrose | 4.605 | 104 | 6.955 | 100 | 1.919 | 98 | 0.825 | 106 |

As shown in Table 17, 18, and 19, it was revealed that trehalose suppressed the formation of scum from "shungiku" (garland chrysanthemum) and spinach and especially the elution of magnesium ion compounds. Trehalose showed the ability of suppressing the elution of magnesium ion compounds from vegetables during the cooking as in the case of meat described in Experiment 11. Referring to the color of garland chrysanthemum and spinach after boiling, boiled vegetables prepared using trehalose kept their green color well in comparison with those prepared without using saccharide and using sucrose.

Experiment 13

Suppressing Effect of Trehalose on the Elution of Magnesium from Boiling Japanese Wheat Noodles Suppressing effect of trehalose on the elution of magnesium was investigated on the boiling of Japanese wheat noodles. Five grams of raw Japanese wheat noodle was added to 40 ml of an aqueous solution comprising 10% (w/w) of trehalose, heated and boiled for two minutes. After stopping the heating and cooling to room temperature, the noodles were removed by filtering with a glass-fiber filter. The resulting filtrate was filled up to give a total volume of 50 ml with water. Among minerals comprised in the filtrate, the amount of only magnesium was measured with the same manner in Experiment 10. A filtrate prepared with no saccharide was used as control. The results of measuring the amounts of magnesium comprised in the filtrates are in Table 20.

TABLE 20

| Saccharide | Magnesium (µg) | Magnesium (%) |
|---|---|---|
| None | 162.6 | 100 |
| Trehalose | 51.9 | 48 |

As shown in Table 20, it was revealed that trehalose suppressed the elution of magnesium ion compounds from Japanese wheat noodles during the boiling. Trehalose showed the ability of suppressing the elution of magnesium ion compounds from Japanese wheat noodles during the boiling as in the cases of meats and vegetables described in Experiment 11 and 12, respectively.

Following examples explain associates of the present invention and their uses in detail.

Example 1

Associate of Trehalose and Calcium Chloride

Figure 5:
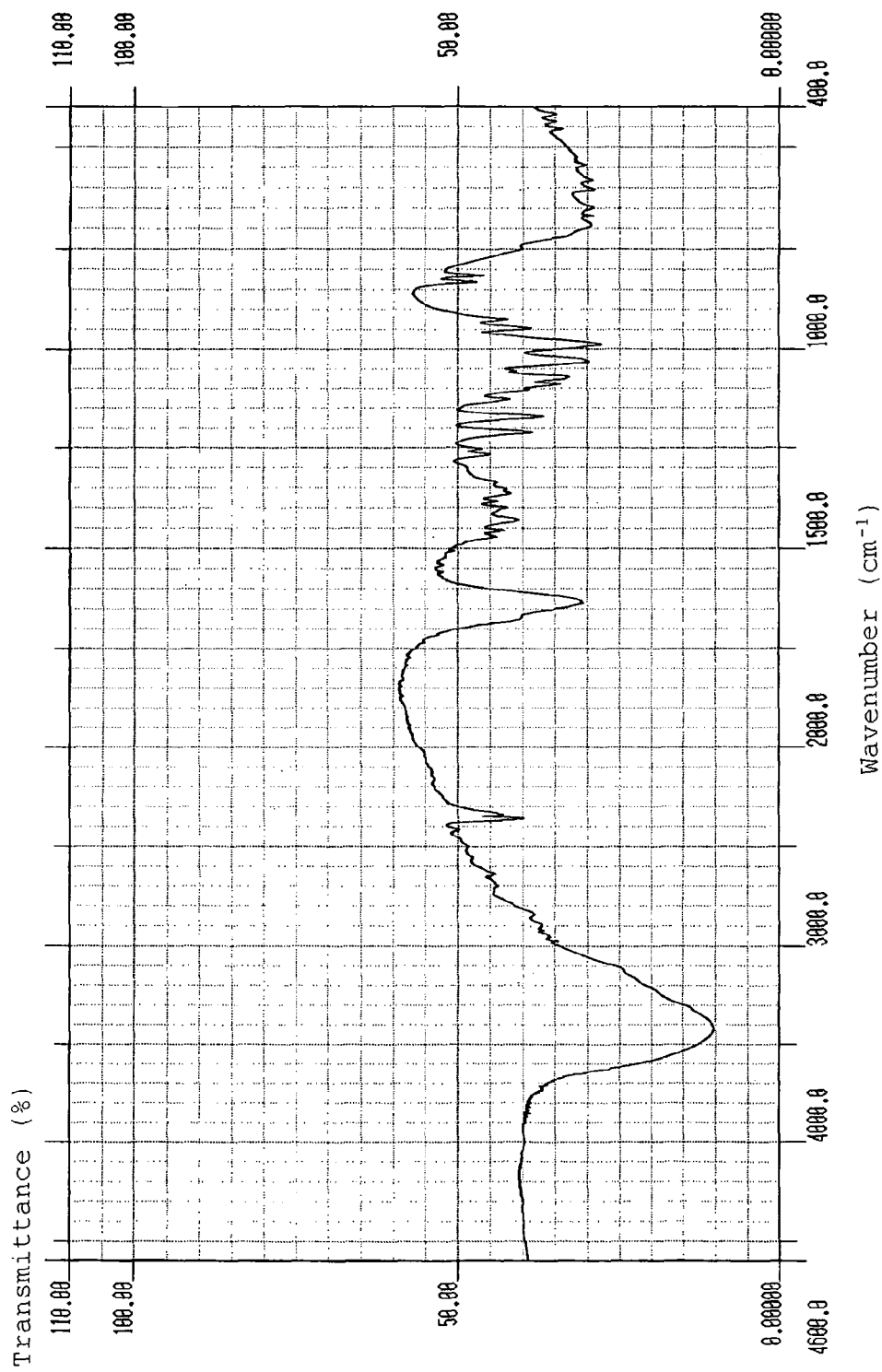
FIG. 5 shows an infrared absorption spectrum of an associate of trehalose and calcium chloride (molar ratio of 1:1).
Figure 6:
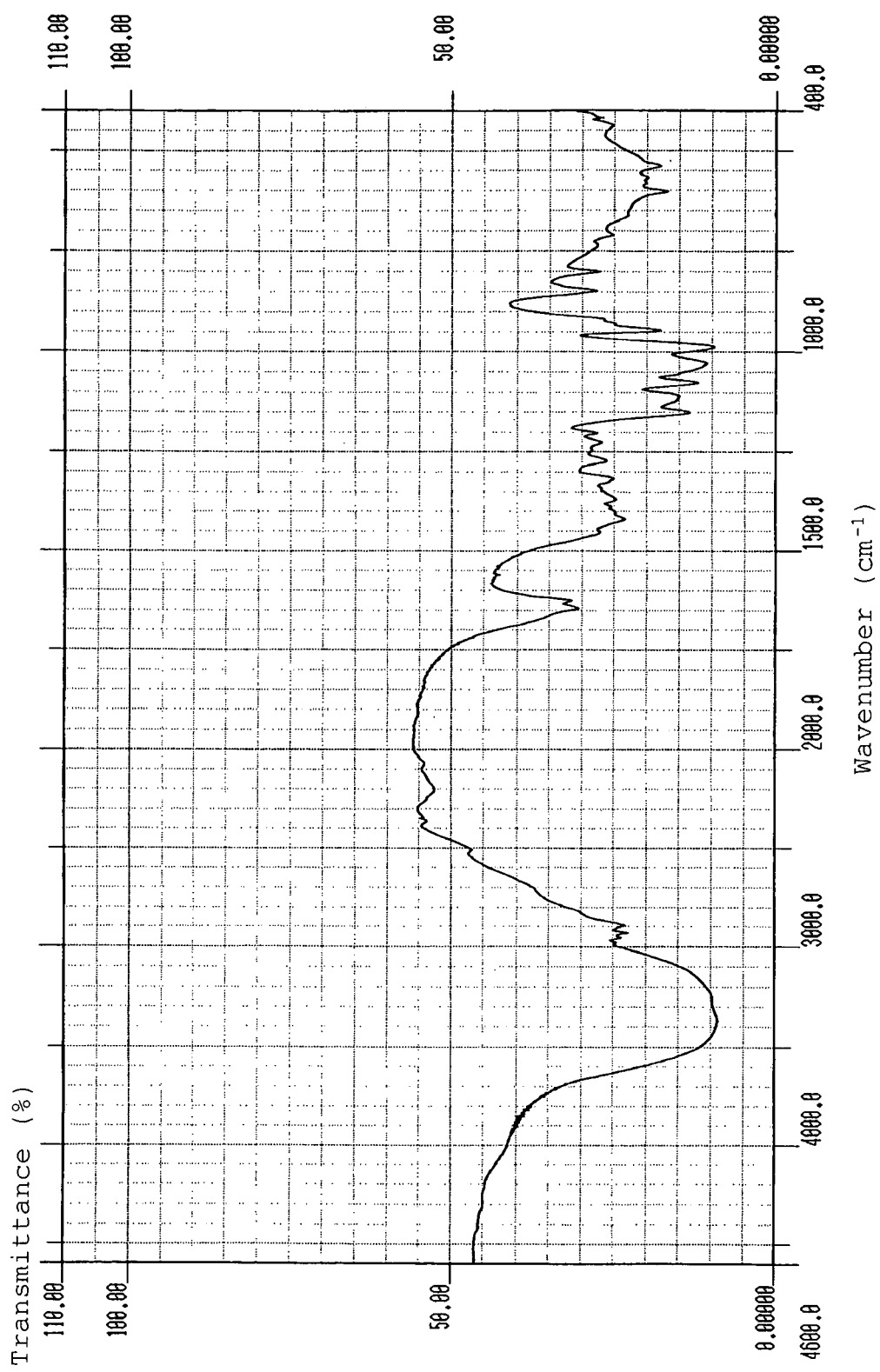
FIG. 6 shows an infrared absorption spectrum of an associate of trehalose and calcium chloride (molar ratio of 1:2).
Figure 7:
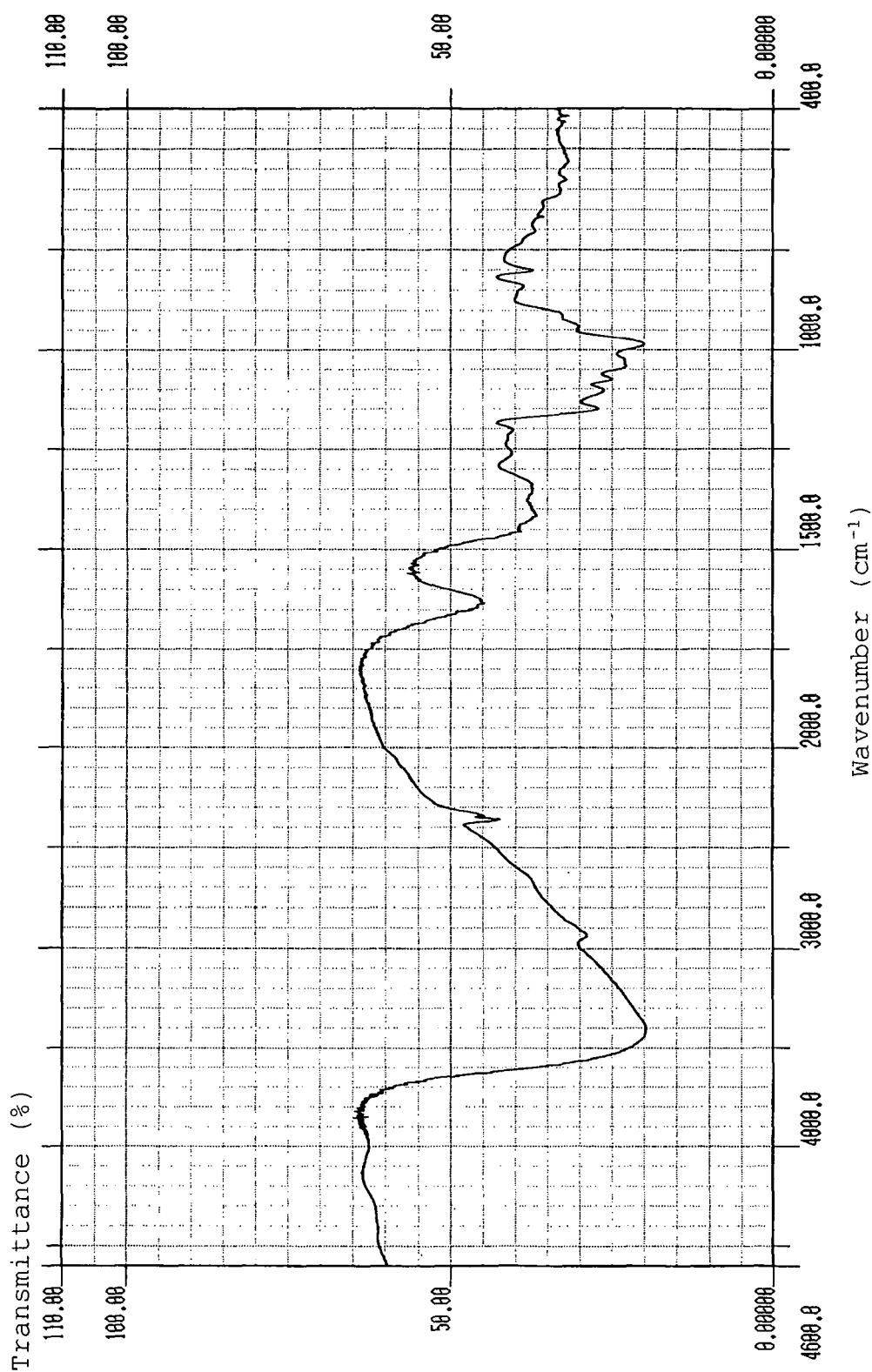
FIG. 7 shows an infrared absorption spectrum of an associate of trehalose and magnesium chloride.
Figure 8:
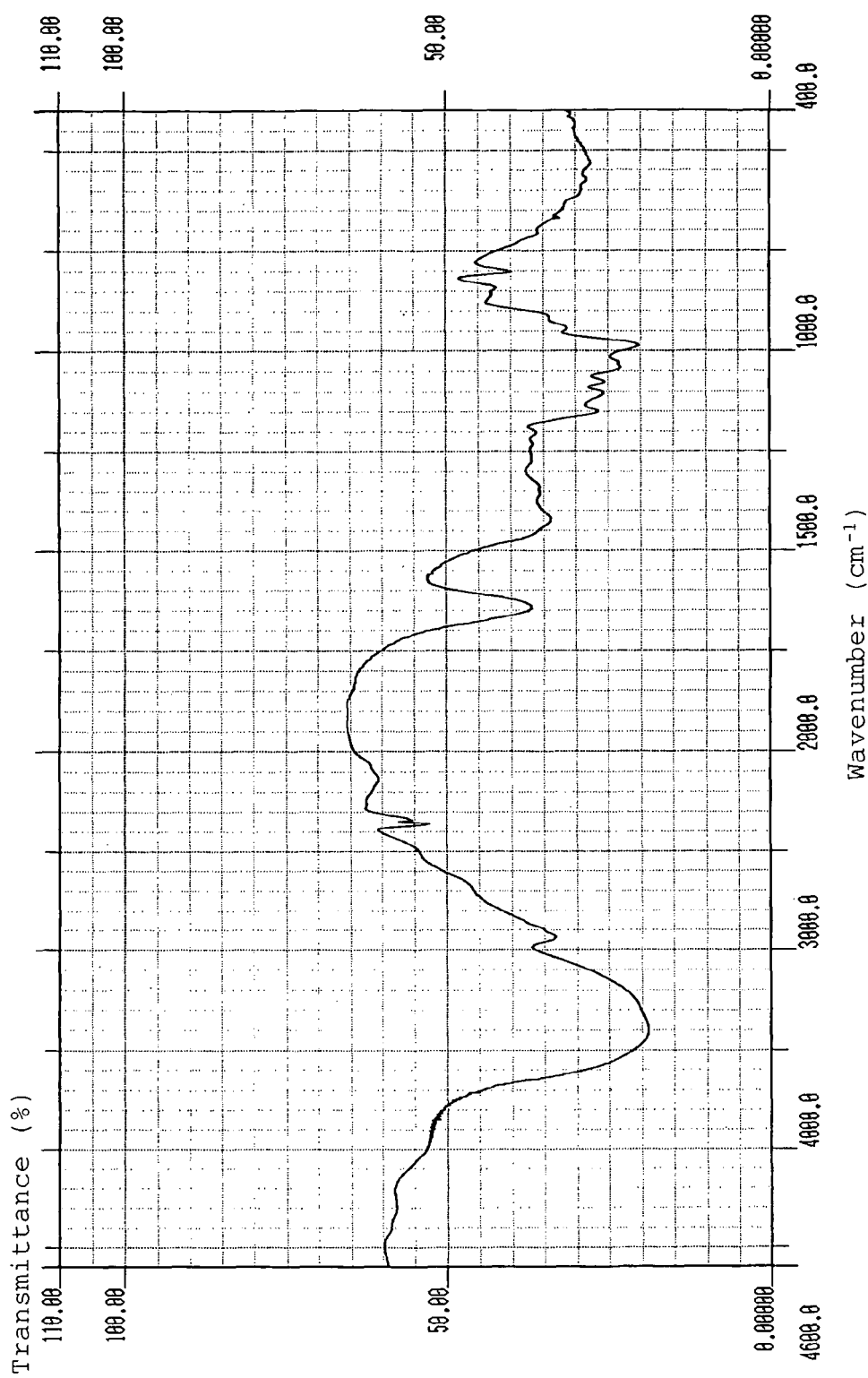
FIG. 8 shows an infrared absorption spectrum of an associate of trehalose and strontium chloride.
Figure 9:
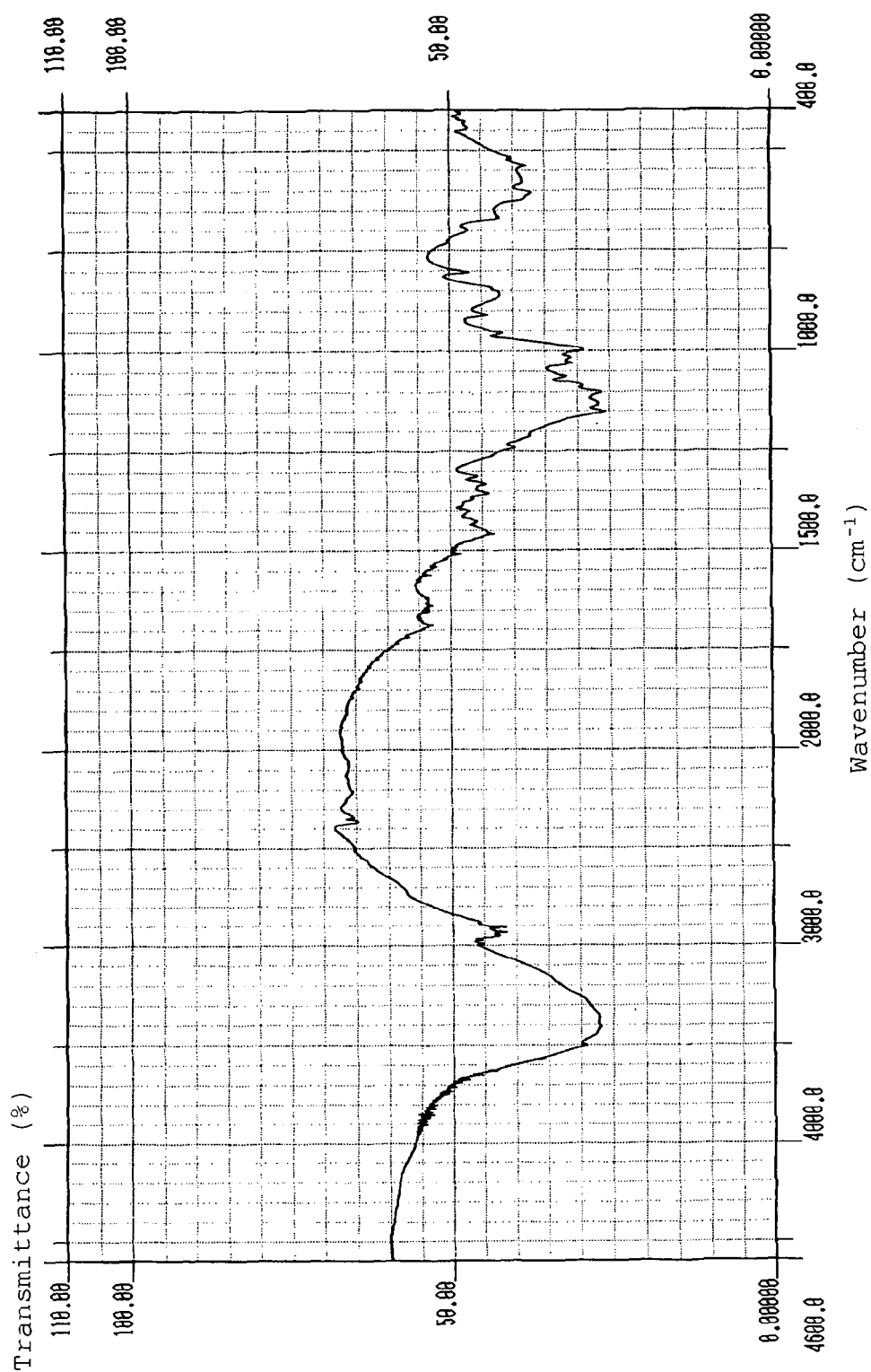
FIG. 9 shows an infrared absorption spectrum of an associate of trehalose and ferrous chloride.
Figure 10:
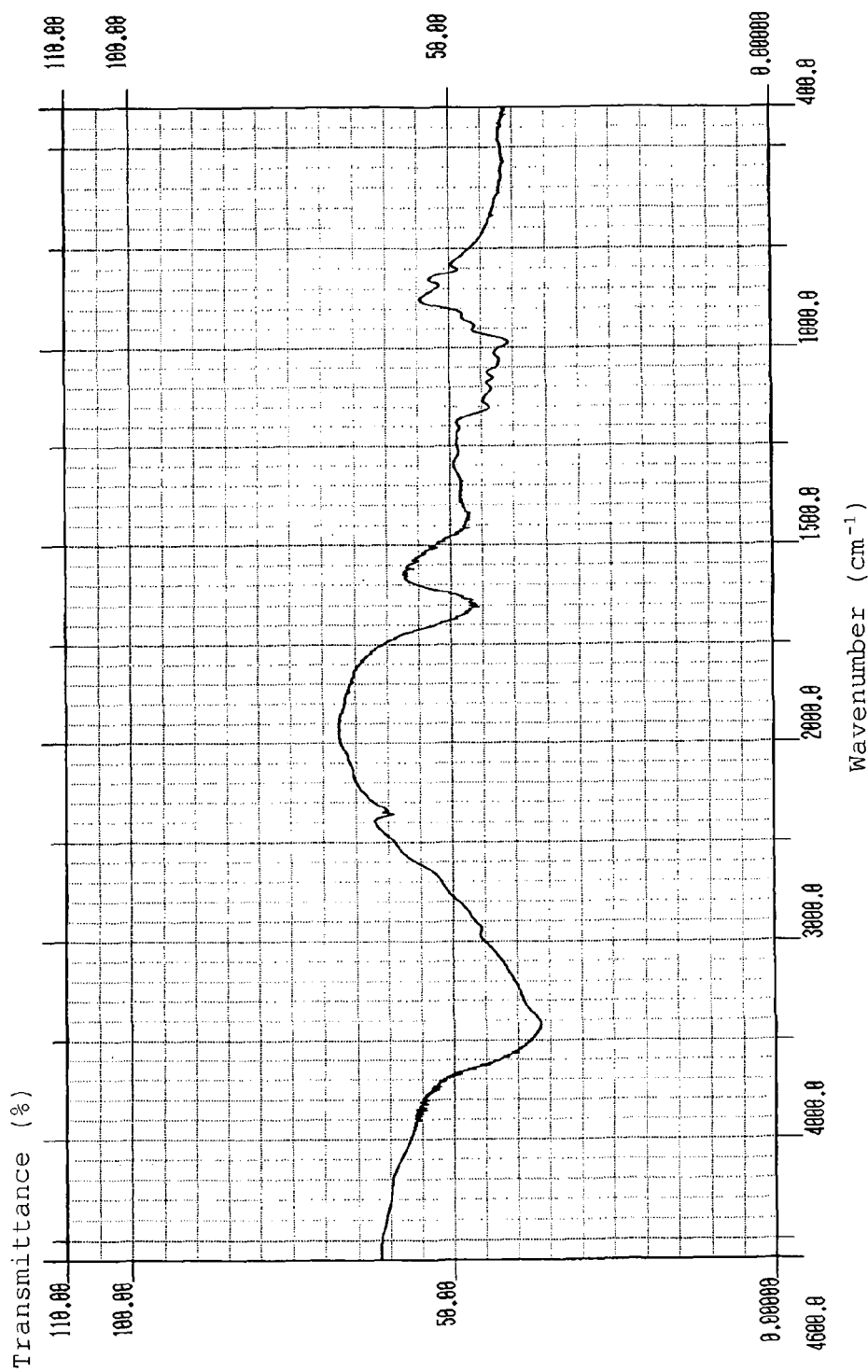
FIG. 10 shows an infrared absorption spectrum of an associate of trehalose and copper dichloride.
Figure 11:
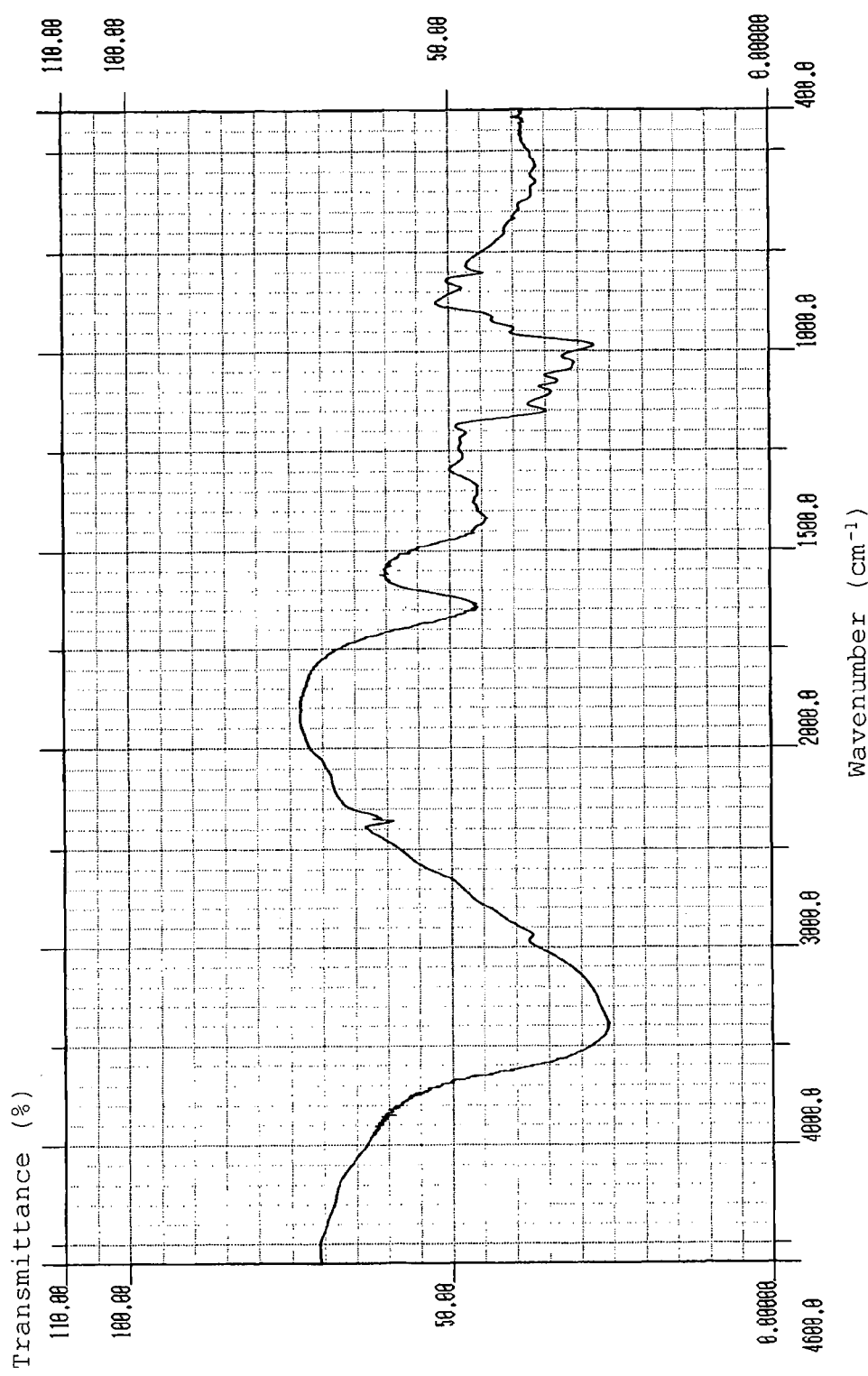
FIG. 11 shows an infrared absorption spectrum of an associate of trehalose and nickel chloride.
Figure 12:
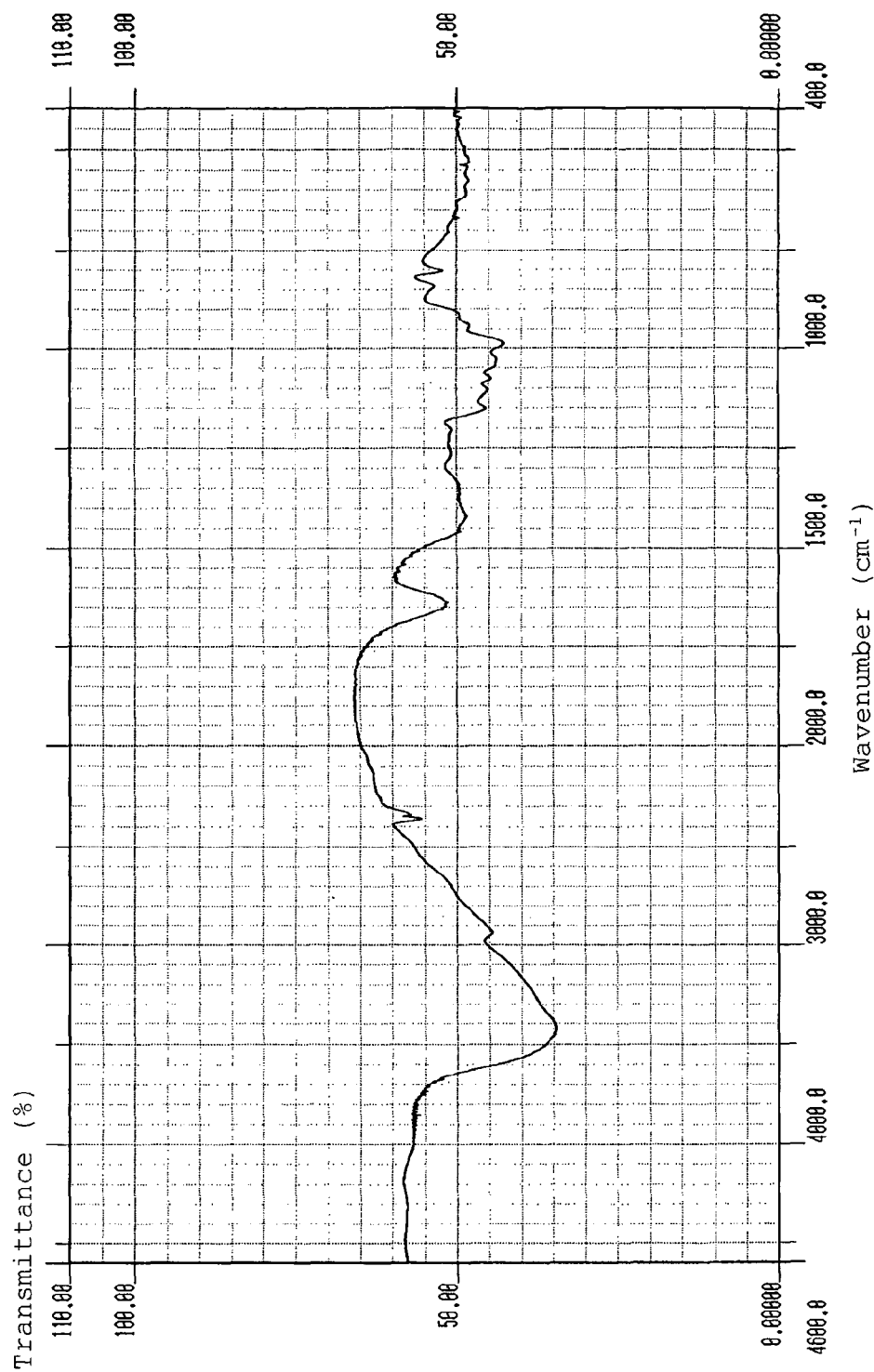
FIG. 12 shows an infrared absorption spectrum of an associate of trehalose and manganese chloride.

According to the method described in Experiment 1-1, crystals of two kinds of associates of trehalose and calcium chloride in molar ratios of 1:1 and 1:2 were prepared. A tablet was prepared conventionally by mixing 2.5 mg either of the preparations with 200 mg of potassium chloride as an excipient and shaping the mixture into a tablet. The infrared absorption spectra of the preparations were measured by using "FT-IR 8200", a Fourier transform infrared spectrophotometer. The results are in FIGS. 5 and 6, respectively.

Since the above products have an improved deliquescence, they have a satisfactory handleability on preserving or admixing with various compositions. Further, since the above products hardly form an insoluble salt, calcium phosphate, when admixed with a composition comprising phosphoric acid, phosphate salt, or phosphate ion, final products, which are prevented from getting cloudy or being precipitated, can be obtained by using the products as materials of aqueous solutions with calcium, such as isotonic drinks, nutritional supplements, and external preparations for the skin. Therefore, the above crystals of the two kinds of associates of trehalose and calcium chloride are very useful for the materials of products with calcium in various fields of foods, cosmetics, pharmaceuticals, etc.

Example 2

Associates of Trehalose and Various Metal Ion Compounds

One part by weight of hydrous crystalline trehalose and equimolars with the trehalose of either of magnesium chloride hexahydrate, strontium chloride hexahydrate, ferrous chloride tetrahydrate, cupric chloride tetrahydrate, nickel chloride hexahydrate, or manganese chloride hexahydrate were mixed, admixed with 0.53 part by weight of deionized water, and dissolved completely by heating. After cooling the resulting each solution, the solution was dried in vacuo at 80° C. for 15 hours. Seven kinds of powdery associates were obtained by pulverizing the resulting dried matters. A part of these samples was sampled respectively and used for infrared absorption spectrum analysis according to the method described in Example 1. The results are in FIGS. 7 to 12, respectively.

Since these associates are improved the solubility in water in comparison with metal ion compounds alone, final products, which are prevented from getting cloudy or being precipitated, can be obtained by using the associates as materials of aqueous solutions with metal ion compounds, such as isotonic drinks, nutritional supplements, and external preparation for skin. Therefore, the associates are very useful for the materials of products with metal ion compounds in various fields of foods, cosmetics, pharmaceuticals, etc.

Example 3

Associates of Maltitol and Various Metal Ion Compounds

Figure 13:
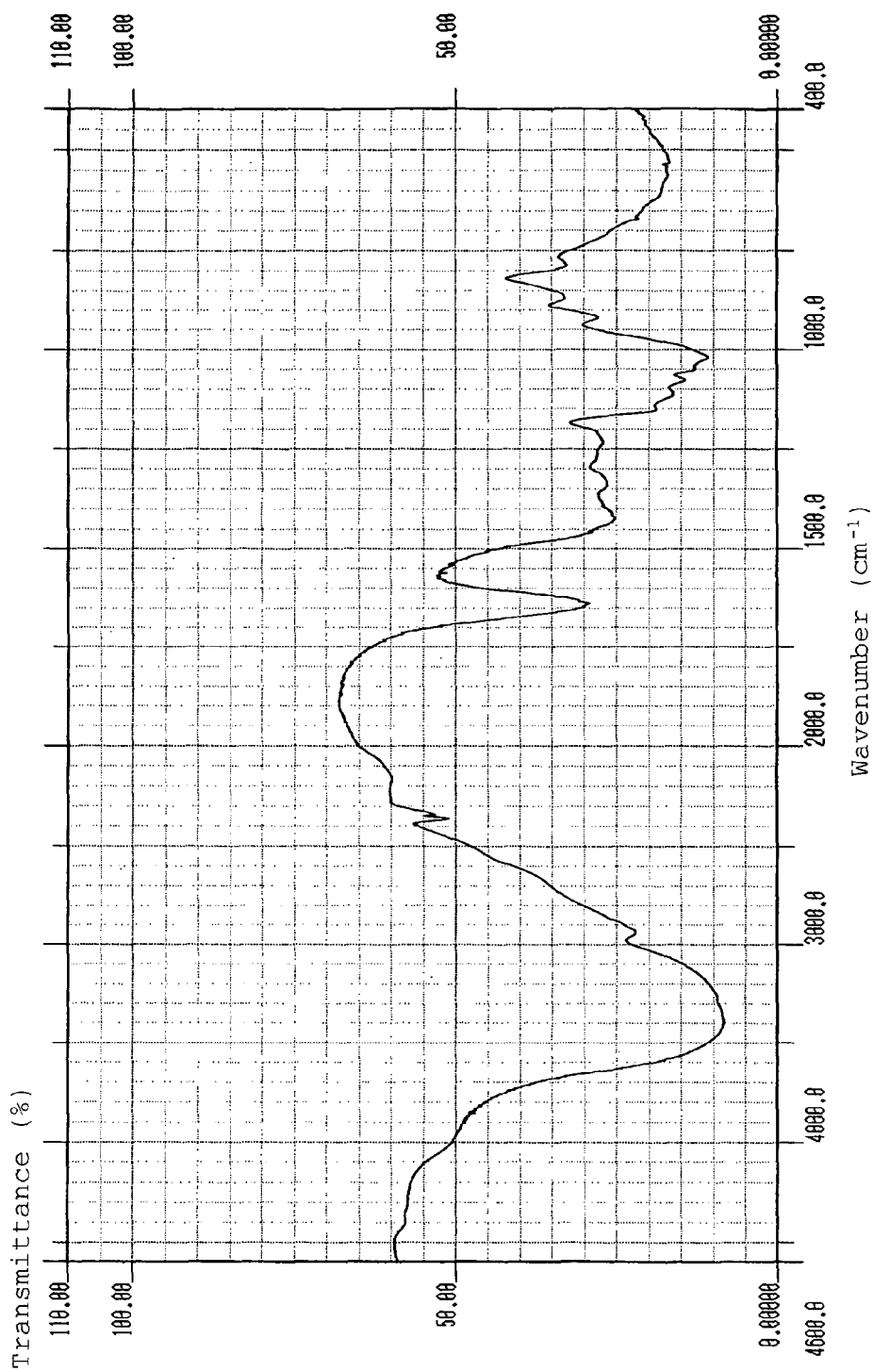
FIG. 13 shows an infrared absorption spectrum of an associate of maltitol and calcium chloride.
Figure 14:
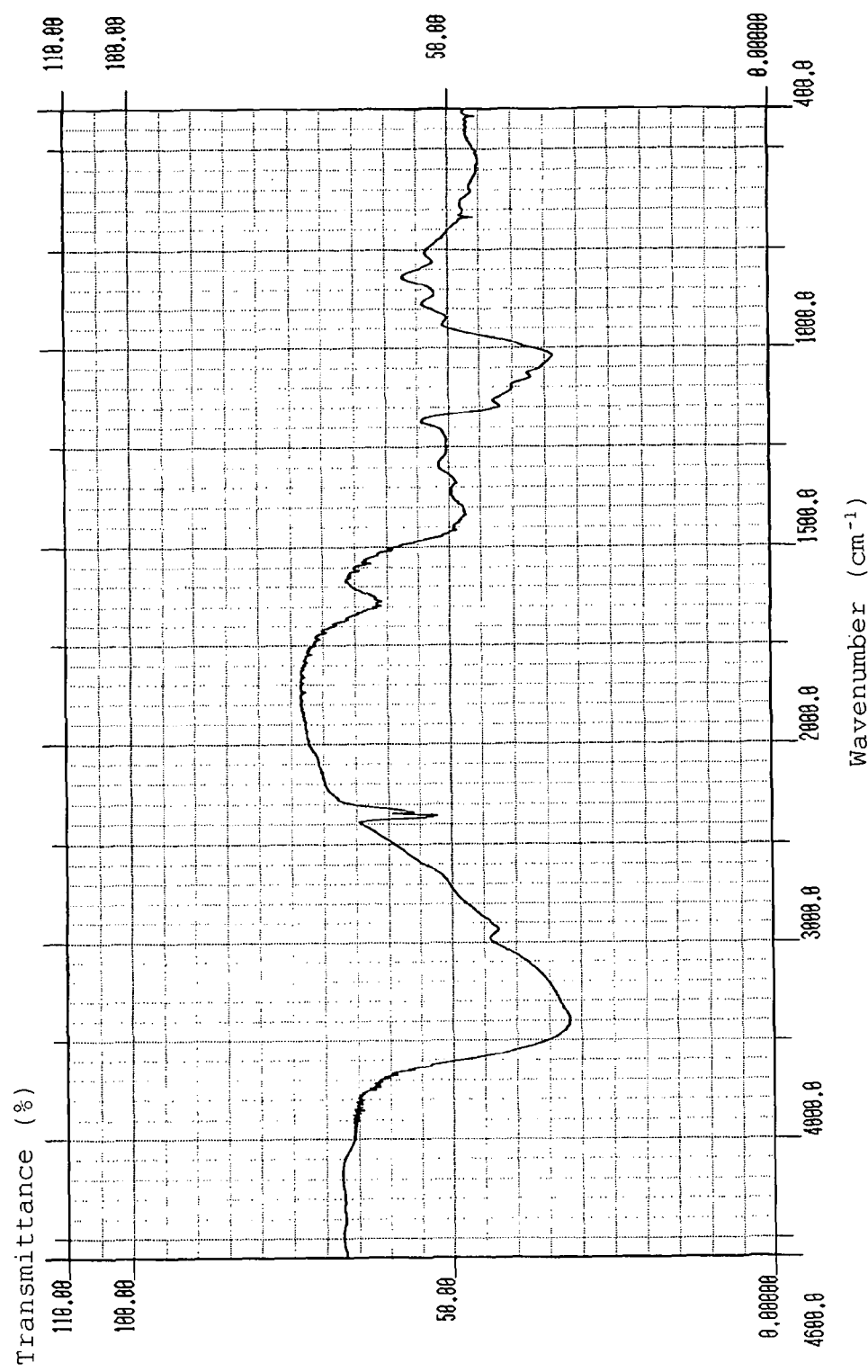
FIG. 14 shows an infrared absorption spectrum of an associate of maltitol and ferrous chloride.

One part by weight of anhydrous crystalline maltitol and equimolars with the maltitol of either of calcium chloride dihydrate or ferrous chloride tetrahydrate were mixed, admixed with 0.53 part by weight of deionized water, and dissolved completely by heating. After cooling the resulting each solution, the solution was dried in vacuo at 80° C. for 15 hours. Two kinds of powdery associates were obtained by pulverizing the resulting dried matters. A part of these samples was sampled respectively and used for infrared absorption spectrum analysis according to the method described in Example 1. The results are in FIGS. 13 and 14, respectively.

Since these associates are improved the solubility in water in comparison with metal ion compounds alone, final products, which are prevented from getting cloudy or being precipitated, can be obtained by using the associates as materials of aqueous solutions with metal ion compounds, such as isotonic drinks, nutritional supplements, and external preparations for the skin. Therefore, the associates are very useful for the materials of products with metal ion compounds in various fields of foods, cosmetics, pharmaceuticals, etc.

Example 4

Powdery Isotonic Drink

According to the formula described below, a powdery composition was prepared by mixing each component sufficiently.

| | |
|---|---|
| Hydrous crystalline trehalose | 6,000 parts by weight |
| Sucrose | 5,000 parts by weight |
| Vitamin B1 | 0.1 part by weight |
| Vitamin B2 | 0.3 part by weight |
| Vitamin B6 | 0.4 part by weight |
| Vitamin C | 200 parts by weight |
| Niacin | 4 parts by weight |
| Disodium phosphate (anhydrate) | 93 parts by weight |
| Potassium phosphate (anhydrate) | 62 parts by weight |
| An associate of trehalose and magnesium chloride prepared by the method of Example 2 | 90 parts by weight |
| An associate of trehalose and calcium chloride (molar ratio 1:2) prepared by the method of Example 1 | 55 parts by weight |

The above powdery composition was divided into 200 ml-plastic bottles attached with screw caps to produce powdery isotonic drinks. The product can be drunk after admixing with about 100 ml of water to 10 grams of the product and dissolving. Since the associates of trehalose and metal ion compounds, comprised in the product, has low deliquescence properties, the product can be preserved for a long period of time. Also, the associates comprised in the product are convenient because they are rapidly dissolved in water. Further, since the associate of trehalose and calcium chloride, comprised in the product, hardly forms insoluble salts from phosphate ion and precipitates when dissolved in water, the product has a character of hardly deteriorating the absorbability of each component when the product solution is drunk after dissolving and leaving for a relatively long time.

Example 5

Skin Lotion (External Lotion for the Skin)

According to the formula described below, a liquid composition was prepared by mixing and dissolving.

| | |
|---|---|
| Citric acid | 0.02 part by weight |
| Sodium citrate | 0.08 part by weight |
| 1,3-Butylenglycol | 2 parts by weight |
| Ethanol | 2 parts by weight |
| Anhydrous crystalline maltitol | 1 part by weight |
| Hydrous crystalline trehalose | 0.2 part by weight |
| L-Ascorbic acid 2-glucoside | 0.5 part by weight |
| An associate of maltitol and ferrous chloride prepared by the method of Example 3 | 0.0035 part by weight |
| Purified water | the rest of above |
| Total | 100 parts by weight |

The above liquid composition was divided into 100 ml-glass bottles attached with screw caps to produce skin lotions. Since the product provides adequate refreshing sense and moisture-retaining ability, it is useful as a basic skin care for keeping the health of the skin. Since associate of maltitol and ferrous chloride, comprised in the product, hardly causes the deterioration of other components, the prescribed effects can be obtained after preserving for a relatively long period of time.

Example 6

Vitamin Supplement

According to the formula described below, a powdery composition was prepared by mixing each component sufficiently.

| | |
|---|---|
| Folic acid | 0.0004 part by weight |
| L-Ascorbic acid | 0.2 part by weight |
| An associate of trehalose and magnesium chloride prepared by the method of Example 2 | 5 parts by weight |
| An associate of trehalose and manganese chloride prepared by the method of Example 1 | 0.008 part by weight |
| Hydrous crystalline trehalose | 5 parts by weight |

The above powdery composition was divided into 80 ml-glass bottles attached with screw caps to produce a vitamin supplement. The product is ingested about 10 grams per day as a rough standard and can be drunk after adding about 100 ml of water or hot water to 10 grams of the product and dissolving. Since associates of trehalose and metal ion compounds, comprised in the product, can be dissolved rapidly in water, the use of the product is very easy.

Example 7

Powder Comprising an Associate of Trehalose and Bittern Components

Figure 15:
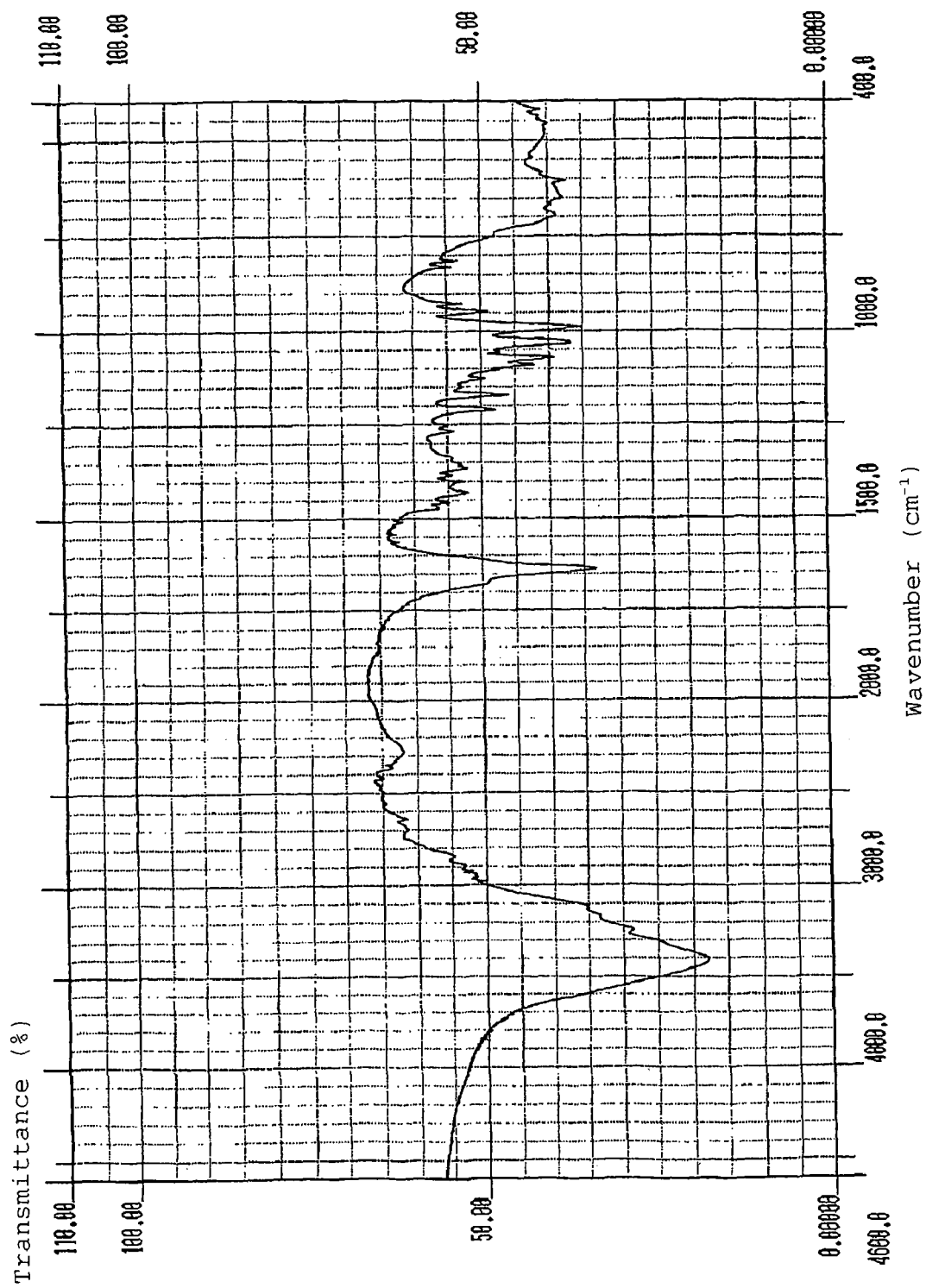
FIG. 15 shows an infrared absorption spectrum of a powder comprising an associate of trehalose and a scum component.

According to the method described in Experiment 2-1, four parts by weight of hydrous crystalline trehalose and 25 parts by weight of a commercially available bittern, commercialized by Sanuki Engyou Co., Ltd., Kagawa, Japan, were mixed and dissolved completely with heating. The resulting solution was dried in vacuo at 60° C. for 15 hours, and then the resulting dried matter was pulverized to produce a powder comprising the associate. According to the method described in Example 1, infrared adsorption spectrum analysis of the product was carried out. The result is in FIG. 15.

Since the product has an improved deliquescence in comparison with a control dried bittern powder prepared by the method of Experiment 4, it has a satisfactory handleability for preserving and admixing with various compositions. Also, since the inherent unpleasant tastes of bittern such as pungent taste and bitter taste were suppressed and improved by forming an associate with trehalose, the product can be used as a mineral-reinforcement comprising relatively large amounts of magnesium and calcium; a material of seasonings, isotonic drinks, nutritional supplements, feeds, and pet foods; and a flavor-improving agent for the production of "ann" (sweetened bean paste), "natto" (fermented soybeans), soymilk, and "tofu" (bean curd); particularly, as a coagulating agent for "tofu" (bean curd). Furthermore, The product is very useful as material of various products in various fields of foods, agricultural and marine products, cosmetics, pharmaceuticals, etc., as reinforcements of minerals such as magnesium and calcium, nutritional supplements for plant, activating agents for plant, moisture-retaining agents, suppressing agent for allergic reaction such as hay fever (pollen disease), and etc.

Example 8

Powder Comprising an Associate of Trehalose and Bittern Components

One part by weight of hydrous crystalline trehalose and one part by weight of a commercially available bittern, commercialized by Sanuki Engyou Co., Ltd., Kagawa, Japan, were mixed and dissolved completely with heating. The resulting solution was sprayed on 300 parts by weight of anhydrous crystalline trehalose, and mixed to produce a dried powder comprising an associate.

Since the product has an improved deliquescence in comparison with a control dried bittern powder prepared by the method of Experiment 4, it has a satisfactory handleability for preserving and admixing with various compositions. Also, since the inherent unpleasant tastes of bittern such as pungent taste and bitter taste were suppressed and improved by forming an associate with trehalose, the product can be used as a mineral-reinforcement comprising large amounts of magnesium and calcium; a material of seasonings, isotonic drinks, nutritional supplements, feeds, and pet foods; and a flavor-improving agent for the production of "ann" (sweetened bean paste), "natto" (fermented soybeans), soymilk, and "tofu" (bean curd); particularly, as a coagulating agent for "tofu" (bean curd). Furthermore, the product is very useful as material of various products in various fields of foods, agricultural and marine products, cosmetics, pharmaceuticals, etc., as reinforcements of minerals such as magnesium and calcium, nutritional supplements for plant, activating agents for plant, moisture-retaining agents, suppressing agent for allergic reaction such as hay fever (pollen disease), and etc.

Example 9

Solution Comprising an Associate of Trehalose and Bittern Components

According to the method described in Experiment 2-1, 144 parts by weight of hydrous crystalline trehalose and 202 parts by weight of a commercially available bittern commercialized by Sanuki Engyou Co., Ltd., Kagawa, Japan, were mixed and dissolved completely with heating. The resulting solution was concentrated under a reduced pressure and then at 60° C. for 15 hours, and then a concentrated solution comprising 63% (w/w) of dry-solid was obtained.

Since the inherent unpleasant tastes of bittern such as pungent taste and bitter taste were suppressed and improved by forming an associate with trehalose, the product can be used as a mineral-reinforcement comprising large amounts of magnesium and calcium; a material of seasonings, isotonic drinks, nutritional supplements, feeds, and pet foods; and a flavor-improving agent for the production of "ann" (sweetened bean paste), "natto" (fermented soybeans), soymilk, and "tofu" (bean curd); particularly, as a coagulating agent for "tofu" (bean curd). Furthermore, The product is very useful as material of various products in various fields of foods, agricultural and marine products, cosmetics, pharmaceuticals, etc., as reinforcements of minerals such as magnesium and calcium, nutritional supplements for plant, activating agents for plant, moisture-retaining agents, suppressing agent for allergic reaction such as hay fever (pollen disease), and etc.

Example 10

Powder Comprising Associate of Maltitol and Bittern Components

Two parts by weight of anhydrous crystalline maltitol and one part by weight of a commercially available bittern were mixed and dissolved completely with heating. The resulting solution was dried in vacuo at 80° C. for 15 hours, and then the resulting dried matter was pulverized to produce a powder comprising an associate.

Since the product has an improved deliquescence in comparison with a control dried bittern powder prepared by the method of Experiment 4, it has a satisfactory handleability for preserving and admixing with various compositions. Also, since the inherent unpleasant tastes of bittern such as pungent taste and bitter taste were suppressed and improved by forming an associate with maltitol, the product can be used as a mineral-supplement comprising large amounts of natural magnesium and calcium; a material of seasonings, isotonic drinks, nutritional supplements, feeds, and pet foods; and a flavor-improving agent for the production of "ann" (sweetened bean paste), "natto" (fermented soybeans), soymilk, and "tofu" (bean curd); particularly, as a coagulating agent for "tofu" (bean curd). Furthermore, The product is very useful as material of various products comprising minerals such as natural magnesium and calcium in various fields of foods, agricultural and marine products, cosmetics, pharmaceuticals, etc.

Example 11

Table Salt

According to the formula described below, solids were prepared by mixing each component sufficiently and drying under a reduced pressure. The resulting solids were pulverized to prepare a powdery table salt.

| | |
|---|---|
| Sodium chloride | 90 parts by weight |
| An solution, comprising an associate of trehalose and bittern components, prepared by the method of Example 9 | 12 parts by weight |

The table salt has a low hygroscopicity and a satisfactory fluidity. Since the unpleasant tastes of bittern such as pungent taste and bitter taste, originated from sodium chloride and bittern components, were suppressed and the product has a good taste by harmonizing sodium chloride, trehalose, and bittern components adequately, the product can be used for cooking and seasoning of foods (including grilled foods) and beverages, and enjoyed the flavor of them. Also, since the product has a similar composition with seawater component, it is a mild salt for living bodies. For example, an aqueous solution, comprising the product at about 3% concentration, can be advantageously used for removing sands from seashells.

Example 12

Seasoned Salt with low in Sodium Chloride

According to the formula described below, a seasoned salt with low in sodium chloride was prepared by mixing each component sufficiently.

| | |
|---|---|
| Sodium chloride | 60 parts by weight |
| Potassium chloride | 9 parts by weight |
| Monosodium L-glutamate | 1 part by weight |
| A powder comprising an associate of trehalose and bittern components, prepared by the method of Example 8 | 5 parts by weight |

The seasoned salt with low in sodium chloride has a low hygroscopicity and a satisfactory fluidity. The bitter taste of the product, originated from the bittern components, is suppressed. Since the product comprises sodium chloride, trehalose, potassium chloride, and monosodium L-glutamate, good taste of the product is increased in addition to the salty taste. The product can be used for seasoning of foods and beverages as well as the conventional products in spite of the product with low in sodium chloride, and enjoyed the flavor of them. Also, the product can be advantageously used for promoting the curing of patients of the circulatory diseases, preventing adult diseases, furthermore, keeping and increasing of beauty and health.

Example 13

"Ann" (Sweetened Bean Paste)

According to the formula described below, "ann" (sweetened bean paste) was prepared by mixing each component and processing.

| | |
|---|---|
| A commercially available white raw "ann" | 1,000 parts by weight |
| Sucrose | 700 parts by weight |
| "SUNMALT-S" (hydrous crystalline maltose) | 100 parts by weight |
| A starchy syrup (75% (w/w) dry solid) | 100 parts by weight |
| A powder comprising an associate of trehalose and bittern components, prepared by the method of Example 8 | 100 parts by weight |
| Agar | 2.5 parts by weight |

Since the "ann" comprises trehalose and bittern components, particularly, magnesium, it has a satisfactory flavor, color and preservability, and a low sweetness. The "ann" is preferable for Japanese confectioneries such as "monaka" (a Japanese cake).

Example 14

Processed Soymilk

Processed soymilk was produced according to the procedure described below. Ten parts by weight of material soybeans were removed the skins. After autoclaving at 130° C. for 10 minutes, 90 parts by weight of hot water was added to the bean with milling. About 60 parts by weight of soymilk was obtained by removing residues (bean curd refuse) from the mixture solution by the centrifugation. Ten parts by weight of maltodextrin (DE (dextrose equivalent) 20), five parts by weight of "SUNMALT®", a powdery crystalline maltose commercialized by Hayashibara Shoji Inc., Okayama, Japan, 0.05 part by weight of table salt prepared by the method of Example 11, 0.02 part by weight of soybean oil, and a suitable amount of lecithin were added to the soymilk and dissolved. A processed soymilk was produced by the steps of sterilizing the above mixture by heating, deodorizing in vacuo, admixing with a suitable amount of flavor, homogenizing, cooling, filling a vessel, and wrapping.

Different from the conventional similar soymilk, the processed soymilk comprises trehalose and a small amount of magnesium. Therefore, it is a quaffable beverage with a good feeling without bitterness, harsh taste, and scratchiness.

Example 15

"Tofu" (Bean Curd)

A "tofu" (bean curd) was produced according to the procedure described below. One part by weight of soybeans were washed with water, soaked in water for 12 hours, and then ground. After adding five parts by weight of water to the ground material and boiling for five minutes, the resulting mixture was filtered with a cloth to produce soymilk. A "tofu" was produced by the steps of adding one part by weight each of pullulan and a powder which comprises an associate of trehalose and bittern components, obtained by the method of Example 7, as a coagulating agent at 70° C. to one hundred parts by weight of the soymilk, coagulating it.

A processing efficiency in the production of the present "tofu" is improved because the time which is required to coagulate the soymilk is prolonged to about seven minutes in comparison with the case of using a bittern. Since the "tofu" comprises pullulan and trehalose, it shows a low syneresis and a high yield and has a satisfactory texture, gloss, and flavor. The product has a satisfactory preservability and can be used to cook chilled "tofu" cut into cubes, boiled "tofu", "miso" soup.

Example 16

Pullulan Film

An aqueous material solution for films, comprising pullulan, was prepared according to the formula described below and removed the bubbles under a reduced pressure. Successively, a pullulan film 30 μm in thickness was prepared by the steps of pouring the solution continuously over a synthetic plastic plate and drying through a hot air with a temperature of 60° C.

| | |
|---|---|
| "PULLULAN PI-20", a pullulan product commercialized by Hayashibara Shoji Inc., Okayama, Japan, | 1,000 parts by weight |
| A sugar ester (sucrose monolaurate) | 1 part by weight |
| A solution comprising an associate of trehalose and bittern components, prepared by the method of Example 9 | 20 parts by weight |
| Purified water | 3,400 parts by weight |

The pullulan film has a satisfactory stability to the change of humidity and solubility in water. Further, the film has a good taste because it comprises an associate of trehalose and bittern components. The film can be used as food and a material for the secondary processing. Furthermore, since the product comprises bittern components, it can be used as a supplement for minerals such as magnesium, calcium, and potassium, and a suppressing agent for allergic reaction such as runny and stuffy noses caused by hey fever (pollen disease).

Example 17

Feed Mixture

According to the formula described below, a feed mixture was prepared by mixing each component.

| | |
|---|---|
| Powdery gluten | 40 parts by weight |
| Skim milk | 38 parts by weight |
| Lactosucrose | 12 parts by weight |
| Vitamin agent | 10 parts by weight |
| Fish meal | 5 parts by weight |
| Calcium diphosphate | 5 parts by weight |
| Liquid fat | 3 parts by weight |
| Calcium carbonate | 3 parts by weight |
| Sodium chloride | 2 parts by weight |
| Powder comprising an associate of maltitol and bittern components, prepared by the method of Example 10 | 2 parts by weight |

The above feed mixture is hardly denatured because a powder comprising an associate of maltitol and bittern components, which is admixed as minerals with the composition, shows no deliquescence. The product has a improved preference for domestic animals and poultry, especially, for pig. The product has a function of promoting the growth of Bifidobacteria and can be advantageously used for preventing infection and diarrhea of domestic animals, promoting appetite and fattening of them, and suppressing smell of their excrement. The product can be optionally mixed with other feed materials, for example, grains, wheat flour, starch, oil cake, and molasses to make rich feeds. Also, the product can be used along with crude feed materials such as straws, hey, bagasse, and corncob to make other feed mixtures.

Example 18

Cosmetic Cream

According to the formula described below, components were mixed and processed to produce a cosmetic cream. Two parts by weight of polyoxyethylenglycol monostearate, five parts by weight of self-emulsified glycerin monostearate, two parts by weight of "αG-HESPERIDINE®", α-glucosyl hesperidin commercialized by Hayashibara Shoji Inc., Okayama, Japan, one part by weight of liquid paraffin, ten parts by weight of glycerin trioctanoate, and a suitable amount of preservative were mixed and dissolved by heating in a usual manner. Two parts by weight of sodium L-lactate, five parts by weight of 13-butylene glycol, two parts by weight of powder comprising an associate of maltitol and bittern components, prepared by the method of Example 10, and 66 parts by weight of deionized water were admixed with the above mixture and emulsified using a homogenizer. The resulting mixture was further admixed with suitable amount of perfume, and stirred to produce a cosmetic cream. The product has a moisture-retaining property because it comprises maltitol and magnesium, and is useful as a sunburn preventive, skin-care agent, and whitening agent.

Example 19

Salve (External Preparation)

A salve (external preparation) was prepared by mixing components according to the formula described below. Two hundred parts by weight of a powder comprising an associate of trehalose and bittern components, prepared by the method of Example 8, 300 parts by weight of maltose, and 50 parts by weight of methanol comprising three parts by weight of iodine were mixed. Further, 200 parts by weight of an aqueous solution containing pullulan in an amount of 10% (w/w) was admixed with the above mixture to produce a salve for curing wounds, which has a adequate spread property and adherability.

Since the product comprises an associate of trehalose and bittern components, it comprises minerals originated from bittern. In addition to the disinfectant activity of iodine, maltose comprised in the product can be used as an energy-supplementing agent for cells. Therefore, the use of the product enables to shorten the curing period and to cure wounds prettily.

Example 20

Nutritional Supplement for Plants

A nutritional supplement for plants in liquid form was prepared by mixing the components according to the formula described below.

| | |
|---|---|
| Diammonium phosphate | 132 parts by weight |
| Ammonium nitrate | 17.5 parts by weight |
| Potassium chloride | 71.5 parts by weight |
| A solution comprising an associate of trehalose and bittern components, prepared by the method of Example 9 | 360 parts by weight |
| Water | 1,000 parts by weight |

The product comprises nitrogen (N), phosphate ($P_2O_5$), potassium ($K_2O$), and magnesium (MgO) in a ratio of 10:20:15:3, respectively. The product has activities of promoting the growth of plants and the running of roots when plants are rooted or replanted, and improving the blooming flowers and the bearing of fruits. The product can be used by properly diluting with water as a nutritional supplement for plants such as crops including grain and potatoes, vegetables, fruit trees, garden plants, trees of garden and roadside, and grasses in golf courses.

Example 21

Bath Agent

A bath agent was prepared by mixing the components according to the formula described below.

| | |
|---|---|
| Sodium bicarbonate | 80 parts by weight |
| Dried sodium sulfate | 12 parts by weight |
| Potassium chloride | 4 parts by weight |
| Sedimentary calcium carbonate | 2 parts by weight |
| Hydrous crystalline trehalose | 50 parts by weight |

-continued

| | |
|---|---|
| "αcG-HESPERIDINE ®", α-glucosyl hesperidine | 2 parts by weight |
| A powder comprising an associate of trehalose and bittern components, prepared by the method of Example 8 | 100 parts by weight |
| Colorings and flavors | proper amount |

Since the product comprises trehalose and magnesium, it has a satisfactory moisture-retaining property and heat-retentive property and is suitable as skin-care agents and whitening agents. The product can be used by diluting 1,000 to 10,000-fold with warm water for taking a bath. The product has a merit of decreasing soap-sediments, scales. Further, the product can be also used as cleansing lotions and lotions by diluting.

Example 22

Soy Sauce

A soy sauce was prepared according to the formula described below. Hydrous crystalline trehalose was added to "TOKUSEN-MARUDAIZU-GENEN-SHOYU", a soy sauce low in salt, commercialized by Kikkoman Co. Ltd., Chiba, Japan, which is not containing trehalose, to give a concentration of 10% (w/w) and dissolved to produce a soy sauce.

Since the product comprises a relatively large amount of trehalose in comparison with a soy sauce not comprising trehalose, it suppresses the formation of scum, particularly, the precipitation of magnesium ion compounds during the cooking of boiled foods and winter cuisine served in the pot. Although the product is a soy sauce low in salt, it can be advantageously used for seasoning boiled foods, daily dishes, roasted foods, and soups, and for enjoying flavors of foods as in the cases of conventional products.

Example 23

"Miso" (Soybean Paste)

A "miso" (soybean paste) was prepared according to the formula described below. Hydrous crystalline trehalose was added to "TAKEYA-MISO-SHIO-HIKAEME", a "miso" low in salt, commercialized by Takeya Miso Co. Ltd., Nagano, Japan, which is not containing trehalose, to give a concentration of 8% (w/w) and mixed to homogeneity to produce a "miso".

Since the product comprises a relatively large amount of trehalose in comparison with a "miso" not comprising trehalose, it suppresses the formation of scum, particularly, the precipitation of magnesium ion compounds during the cooking of boiled foods and winter cuisine served in the pot. Although the product is a "miso" low in salt, it can be advantageously used for seasoning boiled foods, daily dishes, roasted foods, and soups, and for enjoying flavors of foods as in the cases of conventional products.

Example 24

Mineral Water

A mineral water was prepared according to the procedure described below. Hydrous crystalline trehalose was added to ground (spring?) water which was pumped up in a mountain to give the concentration of 0.5% (w/w) and dissolved. The resulting solution was sterilized by filtering with a membrane filter. Sterilized bottles were filled with the filtrate to produce bottled mineral waters. The contents of major metal ion compounds in the mineral water were 40.9 ppm of calcium, 12.5 ppm of sodium, and 11.6 ppm of magnesium.

Since the product comprises trehalose, associates of trehalose and metal ion compounds are formed. The product is not clouded during the preservation for a long period because the solubility of the associates is improved. It is a high quality mineral water, comprising suitable amounts of minerals, with a good feeling, which gives no thirsty.

Example 25

Isotonic Drink

An isotonic drink was prepared by mixing the components and dissolving according to the formula described below.

| | |
|---|---|
| Isomerized sugar (fructose-glucose syrup) | 2 parts by weight |
| Hydrous crystalline trehalose | 3 parts by weight |
| Maltitol | 3 parts by weight |
| Lemon juice | 1 part by weight |
| L-Ascorbic acid | 0.1 part by weight |
| Citric acid | 0.06 part by weight |
| Sodium citrate | 0.03 part by weight |
| Sodium chloride | 0.05 part by weight |
| Monopotassium phosphate | 0.05 parts by weight |
| Calcium lactate | 0.015 part by weight |
| Magnesium chloride | 0.01 part by weight |
| Colorings and flavors | suitable amount |
| Water | 90.685 parts by weight |

Since the product comprises trehalose and maltitol, associates of trehalose and metal ion compounds are formed. The product is not clouded during the preservation for a long period because the solubilities of calcium-organic aid salts are improved. It is a high quality isotonic drink with a good feeling.

Example 26

Dried "Wakame" (Brown Seaweed)

Hydrous crystalline trehalose was added to seawater to give the concentration of 8% (w/w) and dissolved with heating. After blanching the "wakame" in the solution whose temperature was kept to 80-85° C., it was dried to produce a dried "wakame".

Since trehalose and bittern components comprised in seawater form associate on the surface of "wakame", the hygroscopicity of the product after drying was decreased, and the product shows no stickiness caused by the moisture-adsorption during the preservation. The product can be advantageously used as a material for salad and an ingredient for "miso" soup, and hardly forms scum when cooked. Further, The product is useful as foods such as confectionery and food materials.

Example 27

Dried "Kombu" (Tangle)

Hydrous crystalline trehalose was added to seawater to give the concentration of 6% (w/w) and dissolved with ambient temperature. After soaking "kombu" in the solution, it was dried with sunlight to produce a dried "kombu".

Since trehalose and bittern components comprised in seawater form associates, the hygroscopicity of the product after drying was decreased, and the product shows no stickiness caused by the moisture-adsorption during the preservation. The product can be advantageously used as a "kombu" for soup, and hardly forms scum when cooked. The product is a useful food material for "kobujime" (vinegared foods with tangle), "kobumaki" (tangle roll) and "kobucha" (tangle tea), and as foods such as confectionery and food materials.

Example 28

Soap

Soap was prepared by mixing the components to homogeneity according to the formula described below.

| Neat soap obtained from a mixture of beef tallow and palm oil in a weight ratio of 2:1 by saponification-salting out | |
|---|---|
| method | 80 parts by weight |
| Hydrous crystalline trehalose | 10 parts by weight |
| Maltitol | 9 parts by weight |
| L-Ascorbic acid 2-glucoside | 0.5 part by weight |
| Sucrose | 0.5 part by weight |
| "KANKO-SO" NO. 201 | 0.0001 part by weight |
| Flavors | suitable amount |

The product is a high quality soap having a satisfactory foaming property and washing power. The precipitation of hardly soluble salts, particularly, magnesium ion compounds, which are inherently precipitates when dissolving a soap in hard water comprising metal ion compounds, can be suppressed with the product. As a result, the product decreases the formation of soap scum and hardly deteriorates its foaming property and washing power. Further, the product can be advantageously used as soap which prevents body odor and itch because it suppresses the formation of volatile aldehydes and/or the degradation of fatty acids, which are originated from sweat, dirt, and sebum.

Example 29

Toothpaste

Toothpaste was prepared by mixing the components according to the formula described below.

| Calcium phosphate (CaHPO$_4$) | 45 parts by weight |
|---|---|
| Sodium lauryl sulfate | 1.5 parts by weight |
| Glycerin | 25 parts by weight |
| Polyoxyethylenesorbitan laurate | 0.5 parts by weight |
| Hydrous crystalline trehalose | 10 parts by weight |
| Maltitol | 10 parts by weight |
| Preservatives | 0.05 part by weight |
| Water | 13 parts by weight |

The product is improved in unpleasant taste and has a satisfactory availability without decreasing the washing power of detergents. Since trehalose and maltitol, which are comprised in the product, form associates with metal ion compounds, the product has abilities of suppressing the adhesion of tartars and dental plaques, which are formed by calcium and magnesium ion compounds, and promoting the dissolution of them. Therefore, the product has a satisfactory tooth-brushing power.

Example 30

Bouillon for "Nabemono" (Japanese Winter Cuisine Served in Pot)

Bouillon for "Nabemono" (Japanese winter cuisine served in pot) was prepared according to the procedure described below. Two point four parts by weight of "UDON-SOUP", a commercially available powdery "udon" (Japanese wheat noodle) soup commercialized by Higashimaru Shoyu Co., Ltd., Hyogo, Japan, which does not comprise trehalose and ten parts by weight of hydrous crystalline trehalose were admixed with 90 parts by weight of water and dissolved to produce bouillon for "Nabemono" (Japanese winter cuisine served in pot).

Since the product comprises a relatively large amount of trehalose, it suppresses the formation of scum, particularly, the precipitation of magnesium ion compounds from meat and vegetables when "Nabemono" (Japanese winter cuisine served in pot) is cooked. The product also suppresses the elution of magnesium ion compounds from food materials. The product can be advantageously used for cooking boiled foods, "Nabeimono" (Japanese winter cuisine served in pot), daily foods, and soup, and for enjoying the flavor of foods.

INDUSTRIAL APPLICABILITY

As described above, the present invention revealed that both trehalose and maltitol formed associates with metal ion compounds or bittern components by direct interactions in the presence of metal ion compounds or bittern components. Since the associates of the present invention have the improved deliquescence, the high solubility in water, and the decreased reactivity against the oxidation and reduction, they are very useful in their industrial handleability in comparison with conventional metal ion compounds or bittern components. The associates of the present invention can be advantageously used in various fields which use metal ion compounds or bittern components as materials, ingredients, and products, for example, foods (including beverages), agricultural and marine products, cosmetics, pharmaceuticals, commodities, chemical industries, and industries for producing materials or ingredients, which are used in their fields.

The present invention, having these outstanding functions and effects, is a significantly important invention that greatly contributes to this art.

The invention claimed is:

1. A crystalline compound consisting of trehalose, calcium chloride and water, which compound is a crystal constructed of trehalose, calcium chloride and water in a molar ratio of 1:1:1, having main diffraction angles (2θ) of 9.02°, 17.98° and 21.90° by powder X-ray diffraction analysis.

2. A powdery product consisting of equimolar amounts of trehalose or and one or more metal chlorides selected from the group consisting of strontium chloride, ferrous chloride and nickel chloride, which powdery product is produced by:
  (a) forming an associate of trehalose with said metal chloride by mixing said trehalose with one or more of said metal chlorides in equimolar amount of trehalose in a solution; and
  (b) collecting the resulting associate by drying.

3. A powdery product consisting of equimolar amounts of maltitol and ferrous chloride, which powdery product is produced by:
  (a) forming an associate of maltitol with ferrous chloride by mixing said maltitol with ferrous chloride in equimolar amount of maltitol in a solution; and
  (b) collecting the resulting associate by drying.

4. A crystalline compound consisting of trehalose and calcium chloride, which compound is a crystal constructed of trehalose and calcium chloride in a molar ratio of 1:2, having main diffraction angles (2θ) of 12.66° 21.02° and 25.48° by powder X-ray diffraction analysis.

* * * * *